US011992292B2

(12) United States Patent
Akins et al.

(10) Patent No.: US 11,992,292 B2
(45) Date of Patent: May 28, 2024

(54) DIAGNOSTIC SYSTEMS AND METHODS INCLUDING TEMPERATURE-SENSING VASCULAR DEVICES

(71) Applicant: Bard Access Systems, Inc., Salt Lake City, UT (US)

(72) Inventors: Samuel Akins, Draper, UT (US); Gidon Ofek, Millcreek, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 192 days.

(21) Appl. No.: 17/143,965

(22) Filed: Jan. 7, 2021

(65) Prior Publication Data

US 2021/0204818 A1     Jul. 8, 2021

Related U.S. Application Data

(60) Provisional application No. 62/958,299, filed on Jan. 7, 2020.

(51) Int. Cl.
*A61B 5/01*        (2006.01)
*A61B 5/00*        (2006.01)
(Continued)

(52) U.S. Cl.
CPC .............. *A61B 5/01* (2013.01); *A61B 5/0008* (2013.01); *A61B 5/024* (2013.01); *A61B 5/029* (2013.01);
(Continued)

(58) Field of Classification Search
CPC ......... A61B 5/01; A61B 5/6852; A61B 5/029; A61B 5/0008; A61B 2562/0271
See application file for complete search history.

(56) References Cited

U.S. PATENT DOCUMENTS

| 3,739,943 A | 6/1973 | Wilhelmson et al. |
| 3,809,871 A | 5/1974 | Howard et al. |

(Continued)

FOREIGN PATENT DOCUMENTS

| CA | 2897940 A1 | 9/2014 |
| EP | 0331526 A1 | 9/1989 |

(Continued)

OTHER PUBLICATIONS

EP 16849804.6 filed Apr. 11, 2018 Supplementary European Search Report dated Dec. 11, 2018.

(Continued)

*Primary Examiner* — Daniel L Cerioni
(74) *Attorney, Agent, or Firm* — Rutan & Tucker LLP

(57) ABSTRACT

Diagnostic systems and methods including temperature-sensing vascular devices. A diagnostic system can include a catheter assembly for establishing vascular or other access within a body of a patient. The catheter assembly can be equipped with one or more sensors such as temperature sensors that enable monitoring of one or more physiological aspects of the patient, such as temperature, when a portion of the catheter assembly is disposed within the patient. The catheter assembly can be configured to transmit or otherwise forward data relating to the physiological aspects to another location, such as a console, a smartphone or another mobile device, a nurse station, a patient electronic medical record, etc. A method of the diagnostic system can include an instantiating step of instantiating in memory of the console a diagnostic process having one or more functions for at least processing temperature data from the catheter assembly.

10 Claims, 17 Drawing Sheets

(51) Int. Cl.
  *A61B 5/024*  (2006.01)
  *A61B 5/029*  (2006.01)
  *A61B 5/318*  (2021.01)

(52) U.S. Cl.
  CPC ............ *A61B 5/318* (2021.01); *A61B 5/6852* (2013.01); *A61B 5/6876* (2013.01); *A61B 5/7475* (2013.01); *A61B 2562/0271* (2013.01)

(56) References Cited

U.S. PATENT DOCUMENTS

| | | |
|---|---|---|
| 3,985,133 A | 10/1976 | Jenkins et al. |
| 4,078,562 A | 3/1978 | Friedman |
| 4,207,871 A | 6/1980 | Jenkins |
| 4,346,705 A | 8/1982 | Pekkarinen et al. |
| 4,370,983 A | 2/1983 | Lichtenstein |
| 4,373,527 A | 2/1983 | Fischell |
| 4,457,751 A | 7/1984 | Rodler |
| 4,474,309 A | 10/1984 | Solomon |
| 4,484,585 A | 11/1984 | Baier |
| 4,497,324 A | 2/1985 | Sullivan et al. |
| 4,507,974 A | 4/1985 | Yelderman |
| 4,530,696 A | 7/1985 | Bisera et al. |
| 4,533,346 A | 8/1985 | Cosgrove, Jr. et al. |
| 4,573,968 A | 3/1986 | Parker |
| 4,604,093 A | 8/1986 | Brown et al. |
| 4,613,325 A | 9/1986 | Abrams |
| 4,670,007 A | 6/1987 | Wheeldon et al. |
| 4,747,828 A | 5/1988 | Tseo |
| 4,756,706 A | 7/1988 | Kerns et al. |
| 4,785,823 A | 11/1988 | Eggers et al. |
| 4,796,641 A | 1/1989 | Mills et al. |
| 4,809,710 A | 3/1989 | Williamson |
| 4,838,856 A | 6/1989 | Mulreany et al. |
| 4,846,191 A | 7/1989 | Brockway et al. |
| 4,979,940 A | 12/1990 | Bobo, Jr. et al. |
| 4,981,467 A | 1/1991 | Bobo, Jr. et al. |
| 5,000,190 A | 3/1991 | Petre |
| 5,000,664 A | 3/1991 | Lawless et al. |
| 5,024,668 A | 6/1991 | Peters et al. |
| 5,078,683 A | 1/1992 | Sancoff et al. |
| 5,108,364 A | 4/1992 | Takezawa et al. |
| 5,116,312 A | 5/1992 | Blankenship et al. |
| 5,171,301 A | 12/1992 | Vanderveen |
| 5,195,960 A | 3/1993 | Hossain et al. |
| 5,195,967 A | 3/1993 | Nakao et al. |
| 5,275,169 A | 1/1994 | Afromowitz et al. |
| 5,299,571 A | 4/1994 | Mastrototaro |
| 5,304,126 A | 4/1994 | Epstein et al. |
| 5,385,563 A | 1/1995 | Gross |
| 5,395,320 A | 3/1995 | Padda et al. |
| 5,431,627 A | 7/1995 | Pastrone et al. |
| 5,564,425 A | 10/1996 | Tonokura |
| 5,569,186 A | 10/1996 | Lord et al. |
| 5,676,145 A | 10/1997 | Bar-Lavie |
| 5,685,844 A | 11/1997 | Marttila |
| 5,758,643 A | 6/1998 | Wong et al. |
| 5,769,786 A | 6/1998 | Wiegel |
| 5,772,635 A | 6/1998 | Dastur et al. |
| 5,782,805 A | 7/1998 | Meinzer et al. |
| 5,840,068 A | 11/1998 | Cartledge |
| 5,916,153 A | 6/1999 | Rhea, Jr. |
| 5,935,105 A | 8/1999 | Manning et al. |
| 5,984,893 A | 11/1999 | Ward |
| 5,989,222 A | 11/1999 | Cole et al. |
| 6,006,123 A | 12/1999 | Nguyen et al. |
| 6,017,318 A | 1/2000 | Gauthier et al. |
| 6,033,366 A | 3/2000 | Brockway et al. |
| 6,213,972 B1 | 4/2001 | Butterfield et al. |
| 6,296,615 B1 | 10/2001 | Brockway et al. |
| 6,416,291 B1 | 7/2002 | Butterfield et al. |
| 6,659,959 B2 | 12/2003 | Brockway et al. |
| 6,685,668 B1 | 2/2004 | Cho et al. |
| 6,712,771 B2 | 3/2004 | Haddock et al. |
| 6,757,630 B2 | 6/2004 | McClendon et al. |
| 6,770,055 B2 | 8/2004 | Bierman et al. |
| 6,932,114 B2 | 8/2005 | Sparks |
| 6,986,746 B2 | 1/2006 | Fox et al. |
| 6,999,809 B2 | 2/2006 | Currier et al. |
| 7,090,645 B2 | 8/2006 | Fox et al. |
| 7,108,680 B2 | 9/2006 | Rohr et al. |
| 7,138,088 B2 | 11/2006 | Wariar et al. |
| 7,150,735 B2 | 12/2006 | Hickle |
| 7,220,240 B2 | 5/2007 | Struys et al. |
| 7,338,464 B2 | 3/2008 | Blischak et al. |
| 7,471,994 B2 | 12/2008 | Ford et al. |
| 7,473,244 B2 | 1/2009 | Frazier et al. |
| 7,515,954 B2 | 4/2009 | Harlev et al. |
| 7,608,042 B2 | 10/2009 | Goldberger et al. |
| 7,645,258 B2 | 1/2010 | White et al. |
| 7,654,976 B2 | 2/2010 | Peterson et al. |
| 7,654,982 B2 | 2/2010 | Carlisle et al. |
| 7,695,448 B2 | 4/2010 | Cassidy et al. |
| 7,713,241 B2 | 5/2010 | Cartledge et al. |
| 7,729,752 B2 | 6/2010 | Harlev et al. |
| 7,819,817 B2 | 10/2010 | Rahn |
| 7,918,805 B2 | 4/2011 | Chelak |
| 7,927,313 B2 | 4/2011 | Stewart et al. |
| 7,930,018 B2 | 4/2011 | Harlev et al. |
| 7,937,136 B2 | 5/2011 | Harlev et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 8,016,766 B2 | 9/2011 | Goedje et al. |
| 8,034,050 B2 | 10/2011 | Sharareh et al. |
| 8,082,018 B2 | 12/2011 | Duchon et al. |
| 8,092,385 B2 | 1/2012 | Goldberger et al. |
| 8,105,269 B2 | 1/2012 | Zhou |
| 8,105,282 B2 | 1/2012 | Susi et al. |
| 8,163,237 B2 | 4/2012 | Crawford et al. |
| 8,182,445 B2 | 5/2012 | Moubayed et al. |
| 8,200,308 B2 | 6/2012 | Zhang et al. |
| 8,219,413 B2 | 7/2012 | Martinez et al. |
| 8,233,957 B2 | 7/2012 | Merz et al. |
| 8,264,363 B2 | 9/2012 | DelCastillo et al. |
| 8,267,887 B2 | 9/2012 | Mohl |
| 8,287,488 B2 | 10/2012 | Wiegel |
| 8,348,844 B2 | 1/2013 | Kunjan et al. |
| 8,388,582 B2 | 3/2013 | Eubanks et al. |
| 8,425,417 B2 | 4/2013 | Leach et al. |
| 8,433,394 B2 | 4/2013 | Harlev et al. |
| 8,475,448 B2 | 7/2013 | Sharareh et al. |
| 8,500,685 B2 | 8/2013 | Mohl |
| 8,565,857 B2 | 10/2013 | Lips et al. |
| 8,612,257 B2 | 12/2013 | Zaitsu et al. |
| 8,613,753 B2 | 12/2013 | Angel et al. |
| 8,622,989 B2 | 1/2014 | Martin |
| 8,668,712 B2 | 3/2014 | Angel |
| 8,672,875 B2 | 3/2014 | Vanderveen et al. |
| 8,777,977 B2 | 7/2014 | Angel |
| 8,794,830 B2 | 8/2014 | Fang et al. |
| 8,795,203 B2 | 8/2014 | Williams et al. |
| 8,849,382 B2 | 9/2014 | Cox et al. |
| 8,858,185 B2 | 10/2014 | Johnson et al. |
| 8,911,367 B2 | 12/2014 | Brister et al. |
| 8,936,755 B2 | 1/2015 | Gable et al. |
| 8,961,461 B2 | 2/2015 | Stewart et al. |
| 8,974,394 B2 | 3/2015 | Frinak et al. |
| 9,095,653 B2 | 8/2015 | Willmann et al. |
| 9,135,393 B1 | 9/2015 | Blomquist |
| 9,138,533 B2 | 9/2015 | Thompson et al. |
| 9,227,025 B2 | 1/2016 | Butterfield et al. |
| 9,272,086 B2 | 3/2016 | Williams et al. |
| 9,327,072 B2 | 5/2016 | Zhang et al. |
| 9,352,078 B2 | 5/2016 | Roger et al. |
| 9,375,531 B1 | 6/2016 | Lee et al. |
| 9,378,334 B2 | 6/2016 | Lee et al. |
| 9,414,782 B2 | 8/2016 | Braig et al. |
| 9,446,191 B2 | 9/2016 | Zhang et al. |
| 9,468,718 B2 | 10/2016 | Hung et al. |
| 9,501,619 B2 | 11/2016 | Portnoy et al. |
| 9,526,825 B2 | 12/2016 | McTaggart et al. |
| 9,586,001 B2 | 3/2017 | Halbert et al. |
| 9,592,029 B2 | 3/2017 | Buckberry |

(56) References Cited

U.S. PATENT DOCUMENTS

| | | | |
|---|---|---|---|
| 9,814,866 B1 | 11/2017 | Goswami | |
| 10,433,790 B2 | 10/2019 | Ofek et al. | |
| 10,813,589 B2 | 10/2020 | McKinney et al. | |
| 2002/0156417 A1 | 10/2002 | Rich et al. | |
| 2003/0106553 A1 | 6/2003 | Vanderveen | |
| 2003/0195428 A1 | 10/2003 | Brockway et al. | |
| 2004/0051368 A1 | 3/2004 | Caputo et al. | |
| 2004/0167385 A1 | 8/2004 | Rioux et al. | |
| 2005/0197585 A1 | 9/2005 | Brockway et al. | |
| 2006/0015074 A1 | 1/2006 | Lynn | |
| 2006/0135940 A1 | 6/2006 | Joshi | |
| 2006/0229531 A1 | 10/2006 | Goldberger et al. | |
| 2008/0146940 A1 | 6/2008 | Jenkins et al. | |
| 2008/0194988 A1 | 8/2008 | Nakamura et al. | |
| 2009/0005675 A1* | 1/2009 | Grunwald | A61B 5/283 600/467 |
| 2009/0006267 A1 | 1/2009 | Fergusson et al. | |
| 2009/0054754 A1 | 2/2009 | McMahon et al. | |
| 2009/0177090 A1 | 7/2009 | Grunwald et al. | |
| 2009/0221956 A1 | 9/2009 | Abrams et al. | |
| 2009/0234328 A1 | 9/2009 | Cox et al. | |
| 2010/0041973 A1 | 2/2010 | Vu et al. | |
| 2010/0222664 A1 | 9/2010 | Lemon et al. | |
| 2011/0004198 A1 | 1/2011 | Hoch | |
| 2011/0046457 A1 | 2/2011 | Gottlieb et al. | |
| 2011/0092955 A1 | 4/2011 | Purdy et al. | |
| 2011/0105877 A1 | 5/2011 | Wilt et al. | |
| 2011/0144540 A1 | 6/2011 | Shen et al. | |
| 2011/0184266 A1 | 7/2011 | Levin | |
| 2011/0257593 A1 | 10/2011 | Kalpin et al. | |
| 2011/0264044 A1 | 10/2011 | Bartz et al. | |
| 2011/0313394 A1 | 12/2011 | Bobo, Sr. | |
| 2011/0319728 A1 | 12/2011 | Petisce et al. | |
| 2013/0030262 A1 | 1/2013 | Burnett et al. | |
| 2013/0066166 A1 | 3/2013 | Burnett et al. | |
| 2014/0180330 A1 | 6/2014 | Angel et al. | |
| 2014/0207005 A1* | 7/2014 | Bukkapatnam | A61B 5/02028 600/509 |
| 2014/0243688 A1 | 8/2014 | Caron et al. | |
| 2014/0276198 A1 | 9/2014 | Dunung et al. | |
| 2015/0025465 A1* | 1/2015 | Ciavarella | A61B 5/1076 604/164.01 |
| 2015/0335820 A1 | 11/2015 | De Armond et al. | |
| 2016/0213424 A1* | 7/2016 | Ghaffari | A61B 90/30 |
| 2016/0287780 A1 | 10/2016 | Lee et al. | |
| 2016/0287784 A1 | 10/2016 | Straw et al. | |
| 2016/0346462 A1 | 12/2016 | Adams et al. | |
| 2017/0086746 A1 | 3/2017 | Ofek et al. | |
| 2017/0136177 A1 | 5/2017 | Lee et al. | |
| 2017/0143898 A1 | 5/2017 | Grosse-Wentrup et al. | |
| 2018/0256038 A1* | 9/2018 | Shah | A61B 5/026 |
| 2019/0374162 A1 | 12/2019 | Ofek et al. | |
| 2021/0244359 A1* | 8/2021 | Schloesser | G16H 50/20 |

FOREIGN PATENT DOCUMENTS

| | | |
|---|---|---|
| WO | 1989011244 A1 | 11/1989 |
| WO | 1993013709 A1 | 7/1993 |
| WO | 2001074263 A1 | 10/2001 |
| WO | 2001095787 A2 | 12/2001 |
| WO | 2002043789 A2 | 6/2002 |
| WO | 2003011125 A1 | 2/2003 |
| WO | 2003077751 A1 | 9/2003 |
| WO | 2003094715 A1 | 11/2003 |
| WO | 2004007012 A2 | 1/2004 |
| WO | 2004087010 A2 | 10/2004 |
| WO | 2006015230 A2 | 2/2006 |
| WO | 2006055654 A1 | 5/2006 |
| WO | 2006055658 A1 | 5/2006 |
| WO | 2007146864 A2 | 12/2007 |
| WO | 2008032249 A2 | 3/2008 |
| WO | 2010011846 A1 | 1/2010 |
| WO | 2010/022370 A1 | 2/2010 |
| WO | 2010054312 A1 | 5/2010 |
| WO | 2011/094631 A1 | 8/2011 |
| WO | 2012122267 A1 | 9/2012 |
| WO | 2013061280 A1 | 5/2013 |
| WO | 2014/151068 A2 | 9/2014 |
| WO | 2015/074032 A1 | 5/2015 |
| WO | 2017/053882 A1 | 3/2017 |
| WO | 2019/228991 A1 | 12/2019 |

OTHER PUBLICATIONS

Forrester, et al., "Thermodilution Cardiac Output Determination With a single Flow- Directed Catheter", American Heart Journal, vol. 83, No. 3, 1972.

Normann et al., "A Continuous Cardiac Output Computer Based on Thermodilution Principles", Annals of Biomedical Engineering, vol. 17, 1989.

Nova Biomedical: World Leader in Biosensor Technology—Hospital Connectivity Glucose/Ketone Monitoring System. http://www.novabio.uk/statstrip-ketone/. Last accessed Sep. 19, 2016.

PCT/US2016/053566 filed Sep. 23, 2016 International Search Report and Written Opinion dated Dec. 15, 2016.

Taylor, et al., "Understanding Techniques for Measuring Cardiac Output", Biomedical Instrumentation & Technology, May/Jun. 1990.

Temperature monitoring in catheters: "The Bard/BD Standard 400 Series Temperature-Sensing Foley Catheters" ( 2018).

U.S. Appl. No. 15/275,059, filed Sep. 23, 2016 Final Office Action dated Feb. 1, 2019.

U.S. Appl. No. 15/275,059, filed Sep. 23, 2016 Non-Final Office Action dated Aug. 6, 2018.

U.S. Appl. No. 15/275,059, filed Sep. 23, 2016 Restriction Requirement dated Jun. 11, 2018.

U.S. Appl. No. 16/548,642, filed Aug. 22, 2019 Non-Final Office Action dated Feb. 2, 2021.

PCT/US2021/012529 filed Jan. 7, 2021 International Search Report and Written Opinion dated Mar. 26, 2021.

U.S. Appl. No. 16/548,642, filed Aug. 22, 2019 Notice of Allowance dated Jun. 23, 2021.

U.S. Appl. No. 17/486,573, filed Sep. 27, 2021 Notice of Allowance dated Jul. 18, 2023.

* cited by examiner

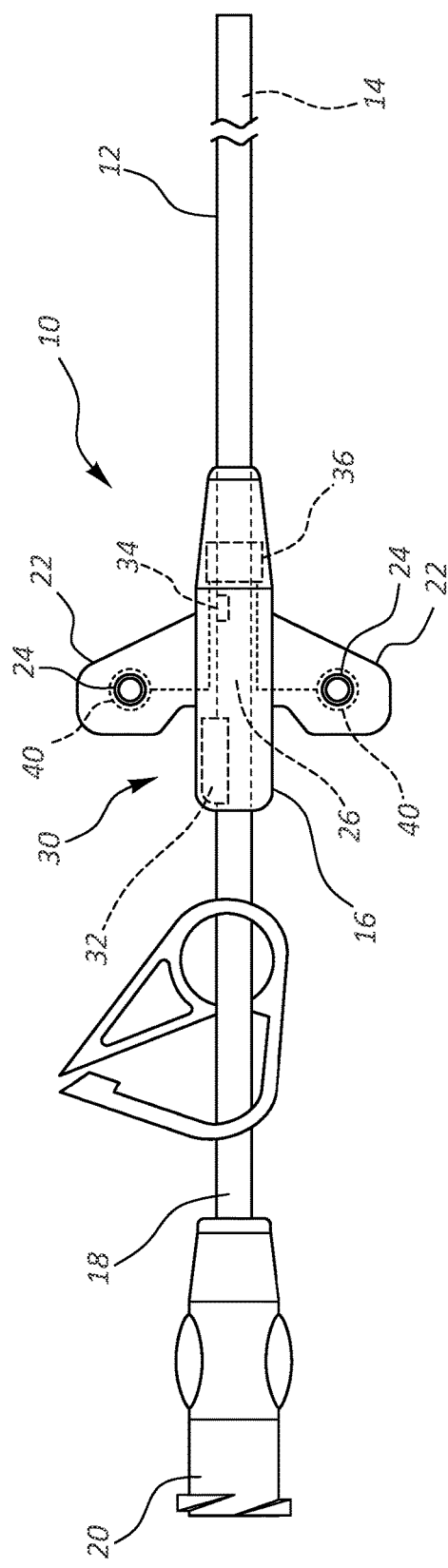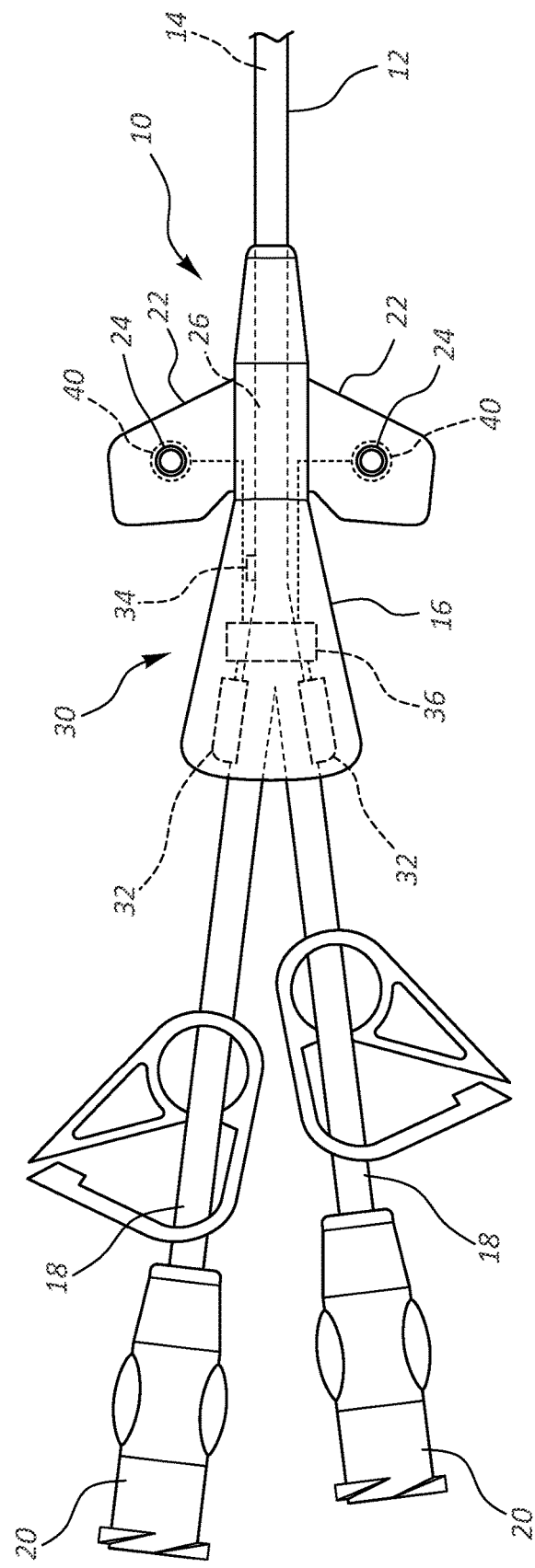
FIG. 1
FIG. 2

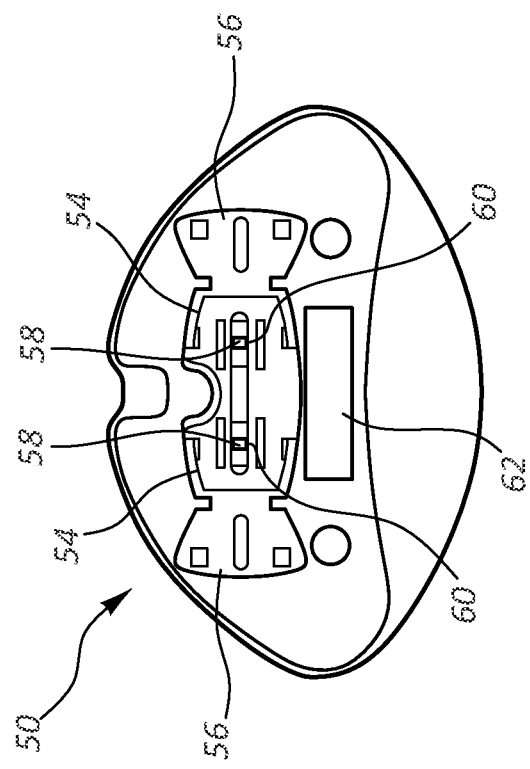
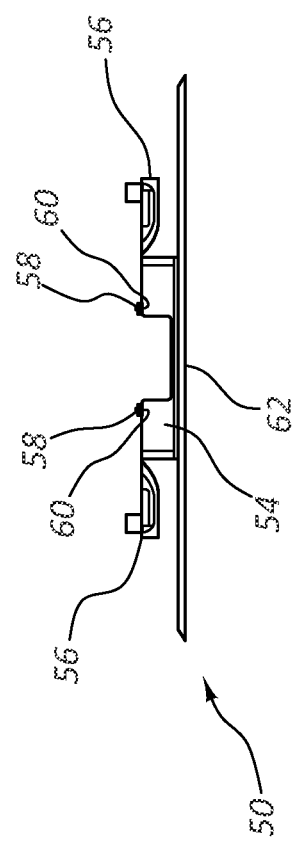
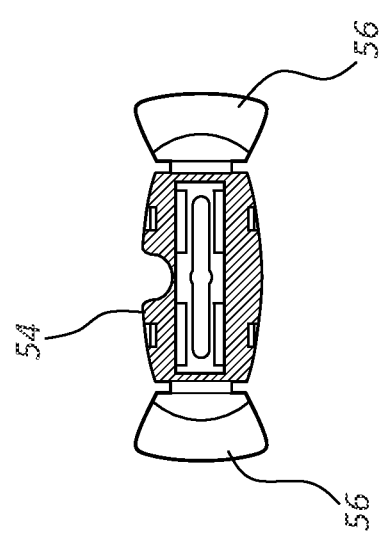
FIG. 4A
FIG. 4B
FIG. 4C

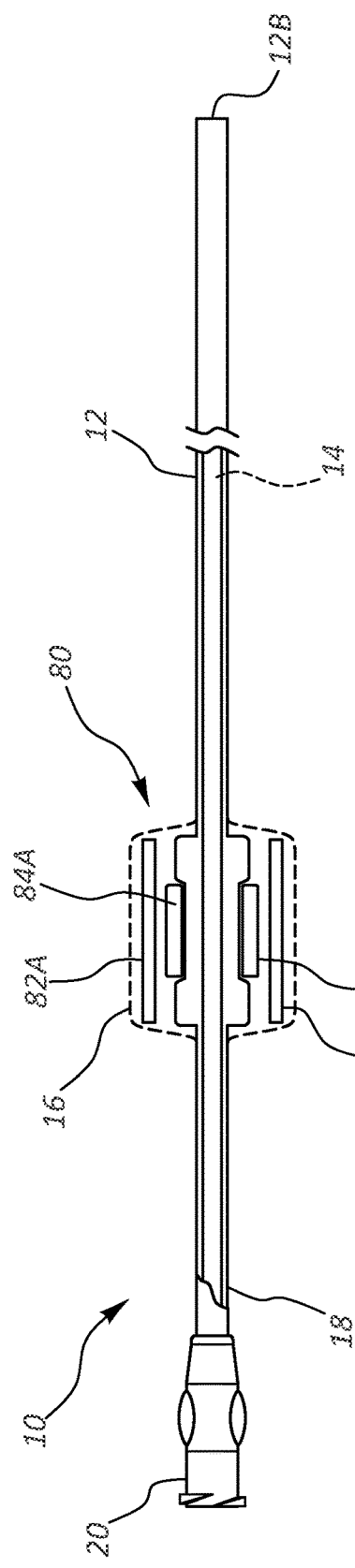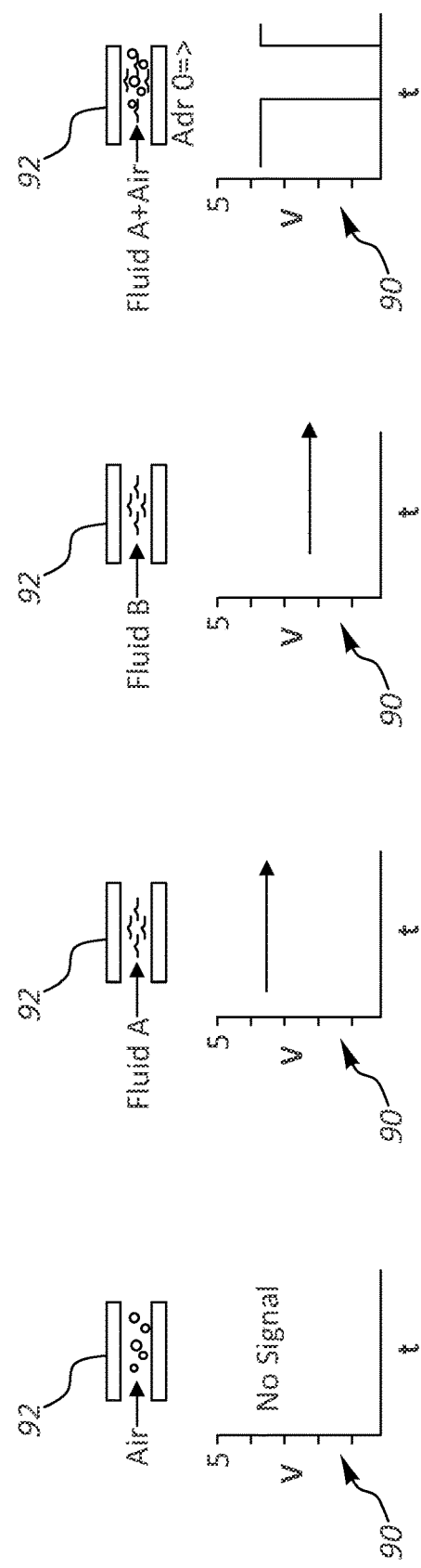
FIG. 7
FIG. 8A  FIG. 8B  FIG. 8C  FIG. 8D

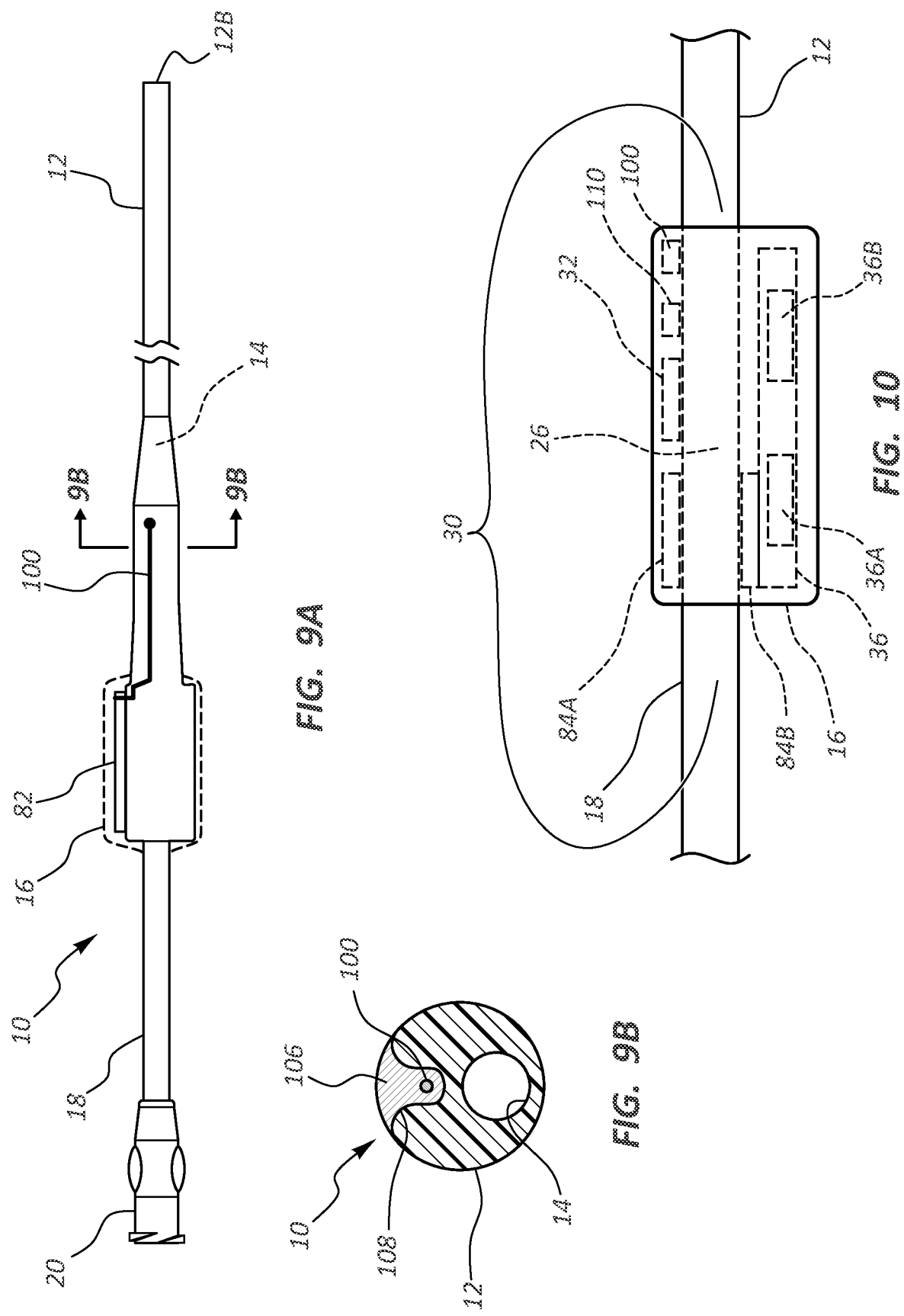

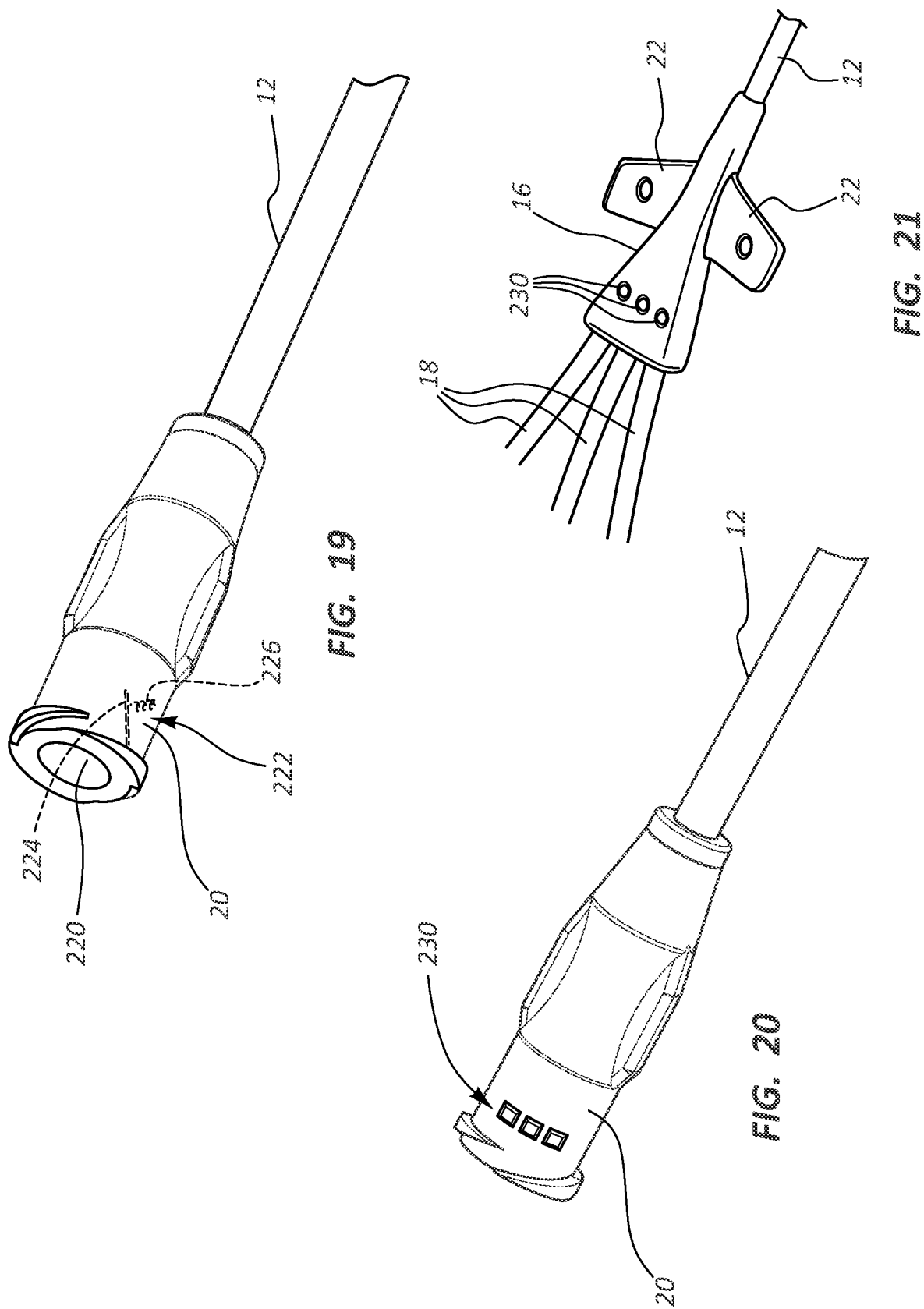

DIAGNOSTIC SYSTEMS AND METHODS INCLUDING TEMPERATURE-SENSING VASCULAR DEVICES

PRIORITY

This application claims the benefit of priority to U.S. Provisional Application No. 62/958,299, filed Jan. 7, 2020, which is incorporated by reference in its entirety into this application.

BACKGROUND

A patient's temperature can be measured by any of a number of existing temperature probes including, but not limited to, skin temperature probes, oral thermometers, tympanic thermometers, esophageal temperature probes, rectal thermometers, temperature-sensing bladder catheters, or the like. While effective, the foregoing temperature probes are typically limited to instantaneously measuring and providing temperature data for a particular tissue at a particular location, which limits the utility of such temperature probes in treating patients. What is needed is a temperature probe with one or more temperature sensors in combination with an enhancing means for enhancing the temperature data to aid in patient diagnosis and expand treatment options.

Disclosed herein are diagnostic systems and methods including temperature-sensing vascular devices that address the foregoing.

SUMMARY

Disclosed herein is a diagnostic system including, in some embodiments, a catheter assembly, a console, and a display screen. The catheter assembly includes a catheter tube, a hub operably attached to the catheter tube, an extension leg operably attached to the hub, and a single temperature sensor or a plurality of temperature sensors. The catheter tube defines at least one lumen extending between a proximal end and a distal end. The hub and extension leg define at least one fluid passageway in fluid communication with the lumen of the catheter tube. The single temperature sensor is disposed within the catheter tube, the hub, or the extension leg configured for temperature measurement therein. The plurality of temperature sensors are disposed within the catheter tube, the hub, the extension leg, or a combination thereof configured for temperature measurement therein. The console is configured to communicate with the catheter assembly. The console includes memory and a processor configured to instantiate a diagnostic process having one or more functions for at least processing temperature data while the catheter tube is disposed in a vasculature of a patient. The display screen is configured to communicate with the console. The display screen is configured to display a graphical user interface ("GUI") including at least a temperature reading associated with the one or more sensors.

In some embodiments, the console is configured to instantiate a display server configured to coordinate input to the console and output from the console. The input includes selection of the one or more functions of the diagnostic process. The output includes the GUI.

In some embodiments, the memory includes one or more temperature data-processing algorithms for processing the temperature data from any temperature sensor of the catheter assembly with the diagnostic process while the catheter tube is disposed in a vasculature of the patient.

In some embodiments, the catheter tube includes the plurality of the temperature sensors. Each temperature sensor of the plurality of temperature sensors is disposed in a different location of a plurality of locations along a length of the catheter tube for measuring a local temperature.

In some embodiments, the memory includes an infection-diagnosis algorithm for diagnosing infection in the vasculature or subcutaneous tissue of the patient with the diagnostic process at any one or more locations of the plurality of the locations along the length of the catheter tube. Diagnosing infection with the infection-diagnosis algorithm is in accordance with local temperature changes or trends thereof of the temperature sensor or the temperature sensors respectively at the one or more locations of the plurality of the locations.

In some embodiments, the catheter tube includes at least one catheter-tube temperature sensor disposed within the catheter tube, at least one hub temperature sensor disposed within the hub, or a combination thereof configured for temperature measurement in the catheter tube, the hub, or both the catheter tube and the hub.

In some embodiments, the one or more functions of the diagnostic process includes a flushing-compliance function. The flushing-compliance function is configured to provide a console-based alert when a flushing-compliant temperature change does not occur at the catheter-tube temperature sensor, the hub temperature sensor, or both the catheter-tube temperature sensor and the hub temperature sensor as expected from room-temperature flushate being flushed through the catheter assembly after patient-temperature blood is drawn from the catheter assembly or at recommended intervals or instances.

In some embodiments, the catheter tube includes a primary catheter-tube temperature sensor disposed within the catheter tube. The console includes a proportional-integral-derivative ("PID") controller communicatively coupled to the primary catheter-tube temperature sensor. The PID controller is configured to maintain the primary catheter-tube temperature sensor at a set number of degrees above blood temperature.

In some embodiments, the one or more functions of the diagnostic process includes a blood-flowrate function. In accordance with the blood-flowrate function, the diagnostic process utilizes a blood-flowrate algorithm to monitor blood flowrate about the primary catheter-tube temperature sensor by way of an amount of power required to maintain the primary catheter-tube temperature sensor at the set number of degrees above blood temperature. The blood flowrate is proportional to the amount of power required to maintain the primary catheter-tube temperature sensor at the set number of degrees above blood temperature.

In some embodiments, the one or more functions of the diagnostic process includes a cardiac-parameter function. In accordance with the cardiac-parameter function, the diagnostic process utilizes the blood-flowrate algorithm in combination with a cardiac-parameter algorithm to determine cardiac parameters including cardiac stroke volume.

In some embodiments, the one or more functions of the diagnostic process includes a catheter-tracking function. In accordance with the catheter-tracking function, the diagnostic process utilizes the blood-flowrate algorithm in combination with a catheter-tracking algorithm to determine when the primary catheter-tube temperature sensor is advanced past a vascular junction in accordance with a volumetric increase in blood flow.

In some embodiments, the diagnostic process is configured to provide catheter-tracking data resulting from the catheter-tracking algorithm as display-server input for display-server output to the GUI of the display screen. The display-server output to the GUI provides a clinician an indication of location of the catheter tube in the vasculature of the patient.

In some embodiments, the catheter tube includes a secondary catheter-tube temperature sensor disposed within the catheter tube proximal of the primary catheter-tube temperature sensor for determining malposition of the catheter tube in the vasculature of the patient.

In some embodiments, the catheter-tracking function is configured to determine malposition of the catheter in accordance with the temperature data from the secondary catheter-tube temperature sensor. The temperature data from the secondary catheter-tube temperature sensor indicates the blood temperature of the patient when the catheter tube is moved against the blood flow. The temperature data from the secondary catheter-tube temperature sensor indicates an elevated blood temperature when the catheter tube is moved with the blood flow on account of the primary catheter-tube temperature sensor being at the set number of degrees above the blood temperature.

In some embodiments, the diagnostic system further includes an electrocardiogram ("ECG") stylet or leads embedded within the catheter assembly. The one or more functions of the diagnostic process include an ECG function for processing ECG data while the ECG stylet is disposed in the catheter tube and the catheter tube is disposed in a vasculature of a patient. The ECG function confirms location of a tip of the catheter tube, monitors migration of the tip of the catheter tube, determines heart rate, or a combination thereof.

Also disclosed herein is a diagnostic system including, in some embodiments, a vascular access device, a console, and a display screen. The vascular access device includes an elongate tube and a single temperature sensor. The elongate tube defines at least one lumen extending between a proximal end and a distal end of the elongate tube. The single temperature sensor disposed within a distal-end portion of the elongate tube is configured for temperature measurement therein. The console is configured to communicate with the vascular access device. The console includes memory and a processor configured to instantiate a diagnostic process having a function for at least processing temperature data while the distal-end portion of the elongate tube is disposed in a vasculature of a patient. The console also includes a PID controller communicatively coupled to the temperature sensor. The PID controller is configured to maintain the temperature sensor at a set number of degrees above blood temperature. The display screen is configured to communicate with the console. The display screen is configured to display a GUI including at least a temperature reading associated with the temperature sensor.

In some embodiments, the function of the diagnostic process is a blood-flowrate function. In accordance with the blood-flowrate function, the diagnostic process utilizes a blood-flowrate algorithm to monitor blood flowrate about the temperature sensor by way of an amount of power required to maintain the temperature sensor at the set number of degrees above blood temperature. The blood flowrate is proportional to the amount of power required to maintain the temperature sensor at the set number of degrees above blood temperature.

In some embodiments, the console is configured to instantiate a display server configured to coordinate input to the console and output from the console. The input includes a local maximum from blood-flowrate data resulting from the blood-flowrate algorithm. The output includes an indication of successful placement of the distal-end portion of the elongate tube in the vasculature of the patient in the GUI on the display screen.

Also disclosed herein is a method of a diagnostic system including, in some embodiments, an instantiating step of instantiating in memory of a console a diagnostic process having one or more functions for at least processing temperature data. The method also includes a sending step of sending the temperature data to the console from a catheter assembly. The catheter assembly has a single temperature sensor disposed within a catheter tube, a hub, or an extension leg of the catheter assembly. Alternatively, the catheter assembly has a plurality of temperature sensors disposed within the catheter tube, the hub, the extension leg, or a combination thereof. The method also includes a loading step of loading the temperature data in the memory. The method also includes a processing step of processing the temperature data with a processor of the console in accordance with the one or more functions for processing the temperature data. The method also includes a displaying step of displaying in a GUI on a display screen configured to communicate with the console at least a temperature reading associated with the one or more sensors.

In some embodiments, the method also includes a monitoring step of monitoring blood flowrate about any temperature sensor of the catheter assembly disposed within a vasculature of a patient with a blood-flowrate function utilizing a blood-flowrate algorithm. The blood flowrate is proportional to an amount of power required to maintain a temperature-sensor temperature at a set number of degrees above blood temperature.

These and other features of the concepts provided herein will become more apparent to those of skill in the art in view of the accompanying drawings and following description, which describe particular embodiments of such concepts in greater detail.

DRAWINGS

FIG. 1 provides a plan view of a catheter assembly in accordance with some embodiments.

FIG. 2 provides a plan view of a catheter assembly in accordance with some embodiments.

FIG. 3 provides a plan view of a catheter assembly in accordance with some embodiments.

FIGS. 4A-4C provide various views of a catheter securement device in accordance with some embodiments.

FIGS. 5A-5C provide various views of a catheter securement device in accordance with some embodiments.

FIG. 6 provides a perspective view of a catheter assembly in accordance with some embodiments.

FIG. 7 provides a partial cross-sectional view of a catheter assembly in accordance with some embodiments.

FIGS. 8A-8D provide various views of an ultrasound signal graph in accordance with some embodiments.

FIGS. 9A and 9B provide various views of a catheter assembly in accordance with some embodiments.

FIG. 10 provides a partial cross-sectional view of a hub of a catheter assembly in accordance with some embodiments.

FIG. 11 provides a view of a smartphone in accordance with some embodiments.

FIG. 12 provides a perspective view of a catheter assembly and an auxiliary device in accordance with some embodiments.

FIG. 13 provides a pressure graph for a catheter assembly in accordance with some embodiments.

FIG. 14 provides a partial cross-sectional view of a pressure-sensing syringe in accordance with some embodiments.

FIG. 15 provides a partial cross-sectional view of a pressure-indicating catheter assembly in accordance with some embodiments.

FIG. 16 provides a view of a distal portion of a catheter assembly in accordance with some embodiments.

FIG. 17 provides a view of a distal portion of a catheter assembly in accordance with some embodiments.

FIG. 18 provides a perspective view of a distal portion of a catheter assembly in accordance with some embodiments.

FIG. 19 provides a perspective view of a Luer connector in accordance with some embodiments.

FIG. 20 provides a perspective view of a Luer connector of a catheter assembly in accordance with some embodiments.

FIG. 21 provides a perspective view of a bifurcation hub of a catheter assembly in accordance with some embodiments.

FIG. 22 provides a simplified view of a pump system for use with a catheter in accordance with some embodiments.

FIG. 23 provides a side view of a pump unit of the pump system shown in FIG. 22.

FIG. 24 provides a block diagram of a diagnostic system including a catheter assembly and a console configured for either wired or wireless communication in accordance with some embodiments.

DESCRIPTION

Figure 3:
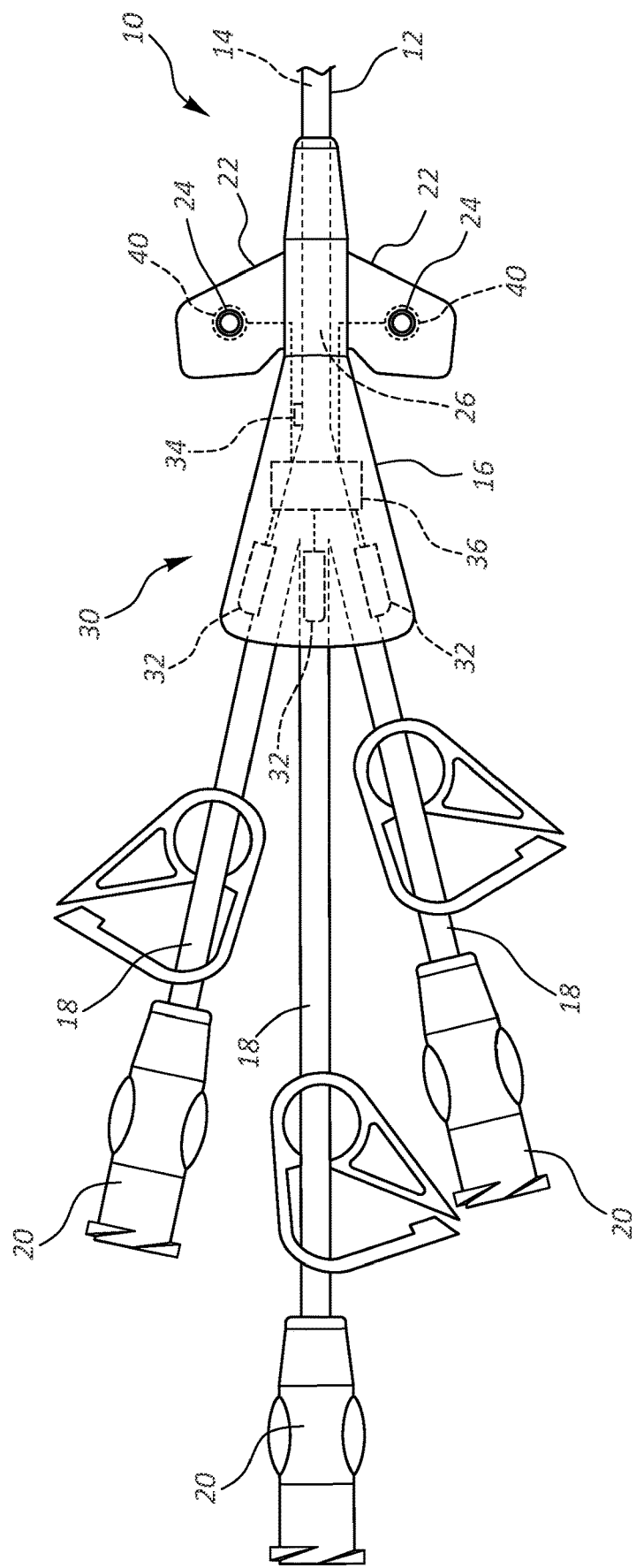

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Disclosed herein are diagnostic systems and methods including temperature-sensing vascular devices such as catheter assemblies and needles for establishing vascular or other access within a body of a patient. The vascular devices and complementary components such as securement devices therefor are described first followed by diagnostic systems including the vascular devices. Lastly, methods of the diagnostic systems are described. Exemplary assemblies, systems, and sensors can be found in U.S. Pat. No. 10,433,790 and U.S. Publication No. 2019/0374162, each of which is incorporated by reference in its entirety into this application.

Vascular Devices and Complementary Components

A vascular access device includes a catheter assembly, a cannula, a needle, or other such medical devices including elongate tubes configured for vascular insertion or placement. A catheter assembly can include a peripherally inserted central catheter ("PICC"), a central venous catheter ("CVC"), an arterial catheter, a Foley-type urinary catheter or the like, a peripheral intravenous ("IV") catheter, a midline catheter, an intermediate-dwell catheter, a feeding tube, or the like, some of which are described in more detail below.

When the vascular access device is a cannula, a needle, or the like having an elongate tube defining at least one lumen extending between a proximal end and a distal end thereof, the elongate tube can include one or more sensors that enable monitoring of one or more physiological aspects or other parameters of a patient, or physical aspects of the vascular access device itself or its operation, when the vascular access device is disposed within a patient. For example, the vascular access device can include a single temperature sensor disposed within a distal-end portion of the elongate tube configured for temperature measurement therein. Additional details for the foregoing are set forth below with respect to catheter assembly-type vascular access devices.

The catheter assembly is equipped with one or more sensors that enable monitoring of one or more physiological aspects or other parameters of the patient, or physical aspects of the catheter assembly itself or its operation, when the catheter assembly is disposed within the patient. Such aspects include central venous pressure, body temperature, ECG heart signals, oxygen levels, ultrasound data, glucose, etc. The sensor(s) included with the catheter assembly are placed so as to enable detection of data related to these or other parameters. In some embodiments, the one or more sensors are disposed in or proximate to a hub of the catheter assembly, though a variety of other locations are also possible. Moreover, other components and structures associated with the catheter assembly, such as a needleless connector for instance, can include one or more sensors for monitoring physiological/physical aspects.

Further, the catheter assembly includes the ability to wirelessly transmit or otherwise forward data relating to the detected physiological aspects/physical aspect to another location, also referred to herein as a receipt location. Examples of data receipt locations include a patient electronic medical record ("EMR"), a patient monitoring apparatus, a smartphone or other mobile device, a tablet, a storage location, a computer server, a nurse station, or a variety of other destinations.

Reference is first made to FIG. 1, which depicts various details of a catheter assembly ("catheter"), generally designated at 10, in accordance with some embodiments. As shown, the catheter 10 includes an elongate catheter tube 12 defining one or more lumens 14 extending between a proximal end and a distal end 13 of the catheter tube 12. The proximal end of the catheter tube is operably connected to a hub 16, which in turn is operably connected to one or more extension legs 18 extending the one or more lumens 14 through a remainder of one or more fluid passageways through the catheter assembly 10. A connector 20, such as a Luer connector, is disposed on a proximal end of the extension leg 18. The hub 16 includes two suture wings 22 that oppositely extend from the body of the hub 16. Each suture wing 22 includes a suture hole 24. Note that the hub 16 can be a bifurcated hub, a trifurcated hub, etc. in accordance with a number of fluid passageways defined therethrough.

In accordance with some embodiments, one or more sensors, also referred to herein as a "sensor array" 30, are included with the catheter 10 to enable the detection of data relating to one or more physiological aspects of the patient or physical aspects of the catheter when the catheter tube 12 is disposed in the vasculature (as discussed here) or other suitable internal portion of the body of the patient. Multiple sensors can be included with the catheter 10, though the number, type, size, placement, function, and desired uses of the various sensors can vary from what is shown and described herein. Note that the sensor array 30 can, in some embodiments, include only one sensor. Note also that, where only one of a particular sensor is discussed below, it is appreciated that more than one of a particular type of sensor can be included, in the same or different locations within the catheter assembly.

As shown in FIG. 1, a pressure sensor 32 is included as part of the sensor array 30. The pressure sensor 32 includes a central venous pressure ("CVP") sensor and is disposed so as enable venous pressure of the patient to be sensed via the fluid (such as blood or saline) typically present within the lumen 14 of the catheter tube 12. As shown, the pressure sensor 32 is disposed within the hub 16 so as to be in operable communication with a fluid passageway 26 within the hub that is in turn in fluid communication with the lumen 14 of the single-lumen catheter tube 12 shown in FIG. 1. Other pressure sensor locations can also be employed, including within the catheter tube 12, the extension leg 18, etc. In some embodiments, the pressure sensor 32 is a medical pressure sensor NPC-100 or NPC-120, manufactured by Amphenol Corporation, though other pressure sensors may also be employed. In some other embodiments, the pressure sensor includes a strain-sensitive Wheatstone bridge. The sensing surface of the pressure sensor 32 can be in direct contact with fluid present in the fluid passageway of the hub 16. Note that the size, shape, and other configuration of the hub 16 may be increased from what is shown and described herein in order to accommodate the sensor array 30.

An ECG sensor 34, also referred to herein as an ECG electrode or electrical sensor, is also included with the catheter assembly to enable ECG signals emanating from the heart of the patient to be detected, in conjunction with an additional ECG sensor/electrode located on the patient's skin or external portion of the catheter assembly/proximate the catheter assembly. As shown, the ECG sensor 34 can be disposed within the hub 16 so as to be in direct contact with fluid present in the hub fluid passageway 26 and the lumen 14 of the catheter tube 12. Other ECG sensor locations can also be employed, including within the catheter tube 12, the extension leg 18, etc. The ECG sensor 34 includes a conductive wire that is able to detect ECG signals of the patient heart that are present in the fluid of the hub fluid passageway 26 and catheter tube lumen 14, though other types of ECG sensors can be employed. Further details regarding a system and method for using an ECG sensor for guiding the catheter assembly to a desired position within the body of a patient can be found in U.S. Pat. No. 8,849,382, entitled "Apparatus and Display Methods Relating to Intravascular Placement of a Catheter," which is incorporated herein by reference in its entirety.

As described, the sensor array 30—including here the pressure sensor 32 and the ECG sensor 34—is disposed within the hub 16, which is sized to provide the needed volume for such sensors. Note that the size, shape, and configuration of the hub 16 can vary from what is shown and described in order to house the sensor(s). The sensors can be located in other portions of the catheter 10, including along or at either end of the catheter tube 12, the extension leg(s) 18, etc. Also note that a variety of sensors for detecting body measurements, physiological aspects of the patient, or physical aspects of the catheter can be included with the catheter assembly, some of which are discussed further below.

FIG. 1 further shows that the hub 16 (or other suitable location) includes a printed circuit board ("PCB") 36 that is configured to govern operation of the sensor array 30, here including the pressure sensor 32 and the ECG sensor 34. The PCB 36 can include a microprocessor for governing sensor operation. The PCB 36 can further include a power source for powering the sensor array 30, though, in some embodiments, the power source can be remotely disposed from the PCB, and even the catheter 10. A non-volatile memory storage location, such as flash memory for instance, can also be included on the PCB 36 to enable data sensed by the sensors of the sensor array 30 to be temporarily or permanently stored thereon. The storage location can be accessible by a user or can be transmitted to a desired location in a manner described below.

The PCB 36 can further include a transmission module, such as a radio for enabling the PCB 36 to transmit sensor data wirelessly to another receipt location, such as those referred to further above. Such wireless transmission can occur via Bluetooth, Wi-Fi, radiofrequency, near-field communication ("NFC"), GPS, ANT, ZigBee, or other manner utilizing electromagnetic radiation. The sensor data can be transmitted from the catheter 10 via a physical connection, such as via a removable physical connection, wires, etc. As mentioned, sensor data, e.g., central venous pressure, ECG signals, temperature, etc., are stored in a memory location included on the PCB 36, or other location on the catheter 10. The PCB 36 can include a clock or timer circuit.

As shown in FIG. 1, the suture holes 24 of the suture wings 22 are configured to include electrical contacts to provide power to the sensors 30 and 34 of the sensor array 30, as well as to the PCB 36. In particular, an annular electrical contact 40 is included in each suture hole 24 of the hub suture wings 22, with the electrical contacts being operably connected to the PCB 36 and sensor array 30. A securement device, such as the securement device 50 shown in FIGS. 4A-4C, is configured to be placed on the skin of the patient and operably connect with and secure in place the catheter 10 once the distal portion of the catheter has been inserted into the patient. To that end, the securement device 50 includes a retainer 54 mounted to an adhesive pad, and securement arms that are hinged so as to removably pivot atop the suture wings 22 of the hub 16 (in a snap-fit arrangement) to secure the hub in place.

The securement device 50 can include additional functionality to provide power to the sensor array 30 and PCB 36. In detail, the securement device 50 includes two posts 58, each of which is configured to serve as an electrical contact 60 and each of which is operably connected with a battery 62, also included in the securement device. The posts 58 are configured to be received within the corresponding suture holes 24 of the catheter suture wings 22 such that electrical contact is established with the electrical contacts 40 of the suture holes. The battery 62 included on the securement device 50 can, in this way, provide electrical power to the sensors 32, 34 and the PCB 36 of the catheter hub 16. Of course, other external power sources can be employed. In some embodiments, electrical contacts between the catheter and the securement device can also be utilized to transfer sensor data therebetween. In some other embodiments, the securement device can include a radio or other mode for transmitting sensor data received from the catheter. In yet other embodiments, the PCB or a sensor can be included on the securement device. It is appreciated that the size, shape, and other configuration of the securement device can vary from what is shown and described herein.

Figure 5A:
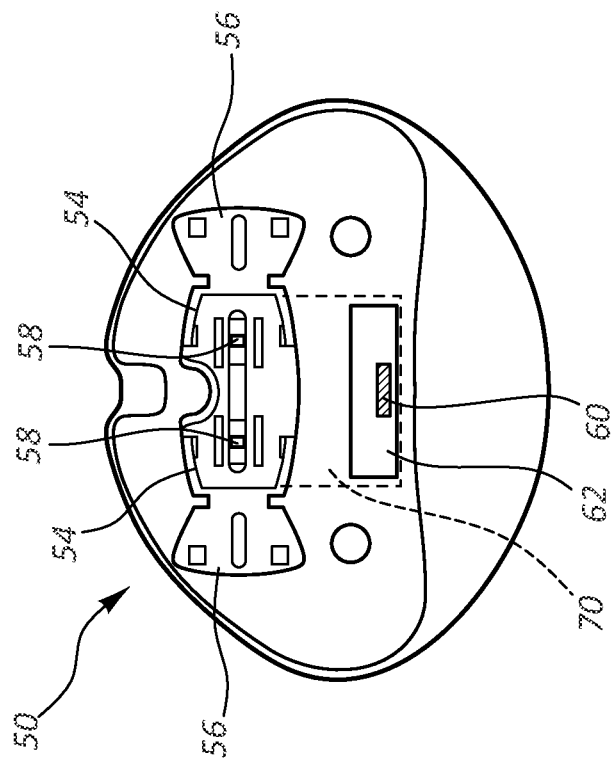
Figure 5C:
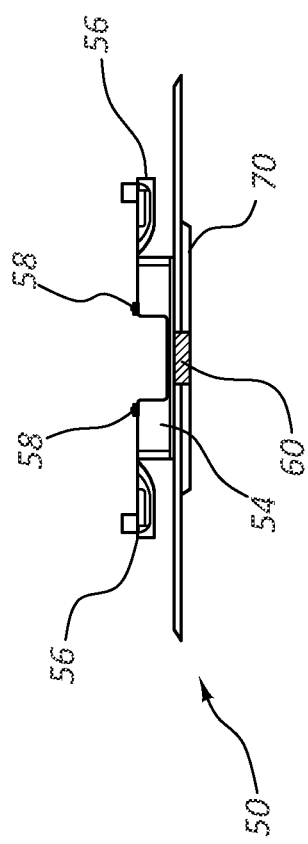
Figure 5B:
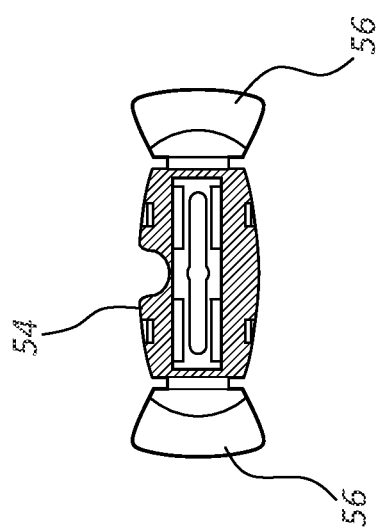

FIGS. 5A-5C depict details of the securement device 50 in accordance with some embodiments, wherein the securement device includes a pod 70 that includes a PCB and a battery for use with the sensor array 30 included on the catheter 10, for instance. This eliminates the need for the PCB or battery to be disposed on the catheter 10 itself. FIGS. 5A and 5C show that the pod 70 includes the electrical contact 60 on an upper surface of the retainer 54, where it is configured to electrically connect with a corresponding electrical contact on the hub 16 of the catheter 10. Thus, when the hub 16 is removably retained by the securement arms 56 of the securement device 50, the sensor array 30 is powered and governed by the battery and PCB of the pod 70. The pod 70 can configured to be removable from the securement device 50, thus enabling it to be reusable with successive securement devices. This may be helpful when the catheter 10 or the securement device 50 are changed out. Thus, the pod 70—including the PCB, battery, or one or more sensors, etc.—can be removed from the securement device and placed in another, thus saving resources and cost. Note also that battery and PCB can be disposed in other locations as well. These and other variations are therefore contemplated. Further details regarding a catheter securement device related to those described herein can be found in U.S. Pat. No. 6,770,055, entitled "Universal Catheter Anchoring System," which is incorporated herein by reference in its entirety.

Additionally, in some embodiments, the securement device 50 can include an ECG sensor (e.g., an electrode) that can cooperate with the ECG sensor 34 of the catheter 10, thus enabling dual ECG signals to be detected and used to determine proximity of the distal end 13 of the catheter tube 12 with respect to the heart. This configuration can also be used to determine malposition of the catheter tube distal end 13, both during initial catheter placement and subsequently during the indwelling of the catheter within the patient. Sensor data from the pressure sensor 30 can also be used in connection with the ECG signals to further detect catheter tube distal end malpositions.

FIGS. 2 and 3 show dual and triple-lumen catheter configurations, respectively, in contrast to the single-lumen configuration of FIG. 1. As with that of FIG. 1, the catheters 10 shown in FIGS. 2 and 3 each include sensor arrays 30 similar to that shown in FIG. 1, including corresponding pressure sensors 32, ECG sensors 34, and PCBs 36. The electrical contacts 40 for electrical connection with electrical contacts 60 of the securement device 50 (FIGS. 4A-4C) are also shown. Note that each extension leg 18 of the catheters 10 in FIGS. 2 and 3 includes a corresponding one of the pressure sensors 32 such that pressure data may be sensed in each extension leg. More or fewer sensors than what is shown in FIGS. 2 and 3 can be employed for sensing physiological aspects of the patient or physical aspects of the catheter assembly including, for instance, lactic acid sensors, oxygen sensors, ultrasound componentry, GPS location sensors, temperature sensors, sizing sensors to measure intraluminal diameter, fluid velocity sensors, glucose meters, oxygen sensors, lactic acid sensors, cardiac output sensors, accelerometers, blood volumetric and cardiac output sensors, etc.

Figure 6:
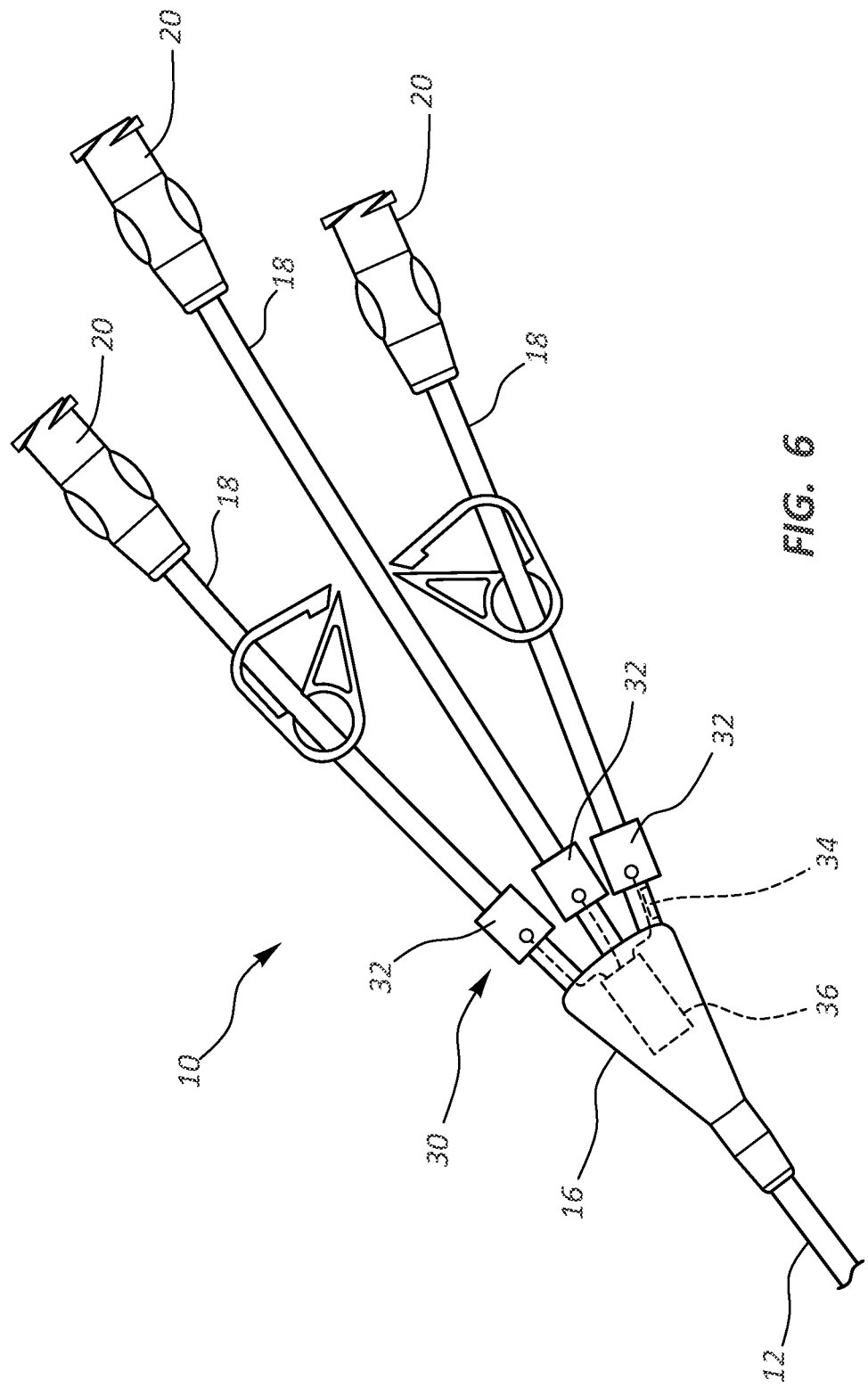

FIG. 6 depicts the catheter 10 including three pressure sensors 30 in specified locations in the corresponding extension legs 18 and an ECG sensor 34 disposed in one extension leg, with each sensor operably connected to the PCB 36 disposed in the hub 16. FIG. 5 thus demonstrates that the number, type, and placement of the sensor(s) and PCB can vary from what has already been shown and described.

FIG. 7 depicts details of the sensor-equipped catheter 10 in accordance with some embodiments, wherein the hub 16 includes an ultrasound assembly 80 comprising upper and lower PCBs 82A and 82B configured to control ultrasound transducers 84A and 84B, respectively. The ultrasound transducers 84A and 84B can be used to ultrasonically evaluate the fluid passageway 26 of the hub 16 to determine the contents of the lumen, as shown in FIGS. 8A-8D. For instance, FIG. 8A shows that when air is present in the fluid passageway 26, no ultrasound signal is present, as depicted in an ultrasound signal graph 90 of FIG. 8A. In contrast, when a fluid, such as fluid A, is present in the fluid passageway 26, the ultrasound transducers 84A and 84B return a signal of a specified voltage consistent with the composition of fluid A, as seen by the graph 90 of FIG. 8B. If a fluid B of differing composition from fluid A is present in the fluid passageway 26, the ultrasound transducer 84A and 84B return a signal of specified voltage consistent with the composition of fluid B, as seen in the graph 90 of FIG. 8C. And when both fluid and air are present in the fluid passageway 26, the graph 90 of FIG. 8D shows that a varying voltage signal is detected by the ultrasound transducers 84A and 84B. In this way, the ultrasound transducers 84A and 84B, coupled with the battery and PCB as discussed further above, can assist the user in determining the presence of particular substances in the fluid passageway 26 of the hub 16, or the lumens of other catheter components, depending on placement of the ultrasound transducers. In some other embodiments, only a single ultrasound transducer is employed.

FIGS. 9A and 9B depict details of the sensor-equipped catheter 10 in accordance with some embodiments, wherein the hub 16 includes a PCB 82 disposed therein and operably connected to a temperature sensor 100, such as a thermocouple, positioned so as to measure core body temperature via blood or other fluids present in the lumen 14 of the catheter. As FIG. 9B shows, the temperature sensor 100 can be placed in proximity to the lumen 14 via a skiving or cavity 108 longitudinally defined in the catheter tube 12 or hub 16. Potting 106 can be optionally used to fill the cavity 108 about the temperature sensor 100. If the temperature sensor 100 (e.g., thermistor) is configured to contact an infusate, the temperature sensor 100 can be used to measure flowrate thereof as described herein for blood flowrate. When used in conjunction with pressure determining means disclosed herein, a more accurate detection of occlusion is possible. In some embodiments, the temperature sensor 100 includes a series 400 Model 401 thermistor available from Cole-Palmer Inc., Vernon Hills, IL.

FIG. 10 shows that a variety of sensors can be included as part of the sensor array 30 within the hub 16 or other suitable location. As depicted in FIG. 10, the hub 16 can include disposed therein the pressure sensor 32, the PCB 36 (including a processor 36A and a wireless communication module 36B), upper and lower ultrasound transducers 84A and 84B, a temperature sensor 100, and an oxygen sensor 110. The various sensors are arranged as needed in proximity to the fluid passageway 26 of the hub 16 so as to sense the relevant parameters as detected in the fluid present in the fluid passageway. The particular arrangement of the sensors can vary from what is shown here.

Figure 11:
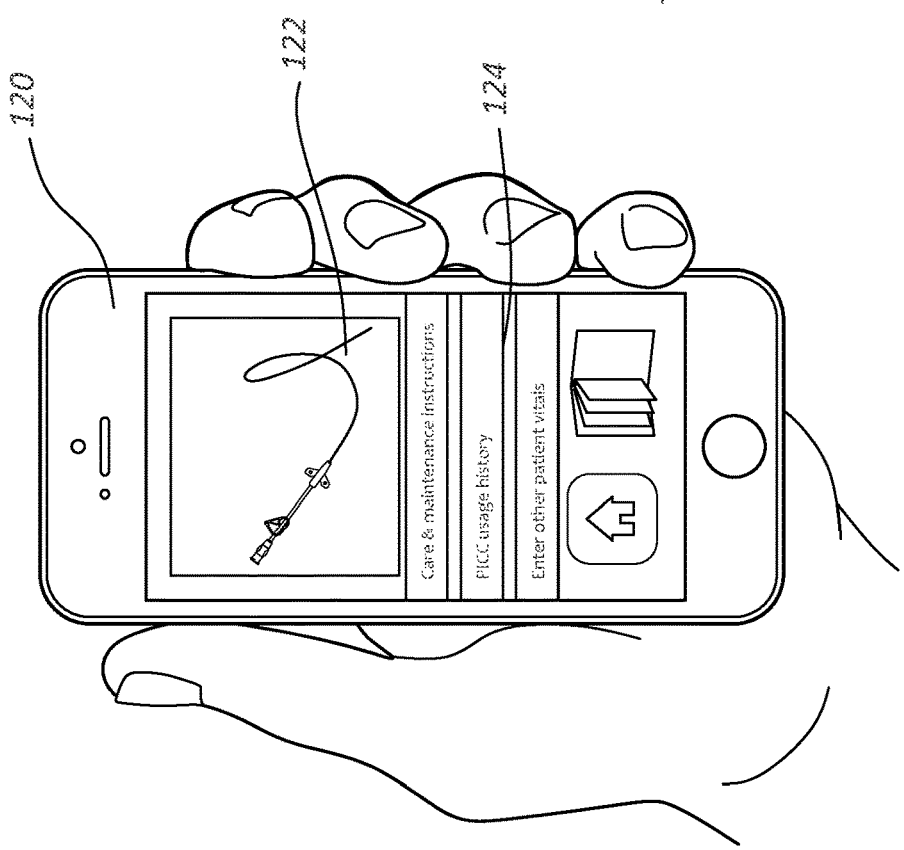

FIG. 11 shows that a smartphone 120 can be the receipt location for wirelessly receiving data from one or more of the sensors of the sensor array, as discussed in some embodiments above. Examples of wireless modes by which the data can be transmitted include Bluetooth, Wi-Fi, radiofrequency, near-field communication (NFC), ANT, ZigBee, etc. Such data transmission can be relayed through a software-based application or other intermediary device. This enables a clinician to receive mobile updates and other sensor data 124 from the catheter 10 via a display screen 122 of the smartphone 120 (or by other mediums including sound, vibration, etc.) in order to be able to monitor the progress or condition of the patient. Other locations for receipt of the sensor data as described above include a patient electronic medical record ("EPR"), a patient monitoring apparatus, other mobile devices including electronic tablets and laptop computers, an electronic storage location, a computer server, a nurse station, medical equipment such as a pump attached to the catheter, and a variety of other destinations. It is appreciated that devices, components, computers, etc. that are located at the receipt location can perform operations on the received data, including analysis, trending, alarm functions, etc.

Figure 12:
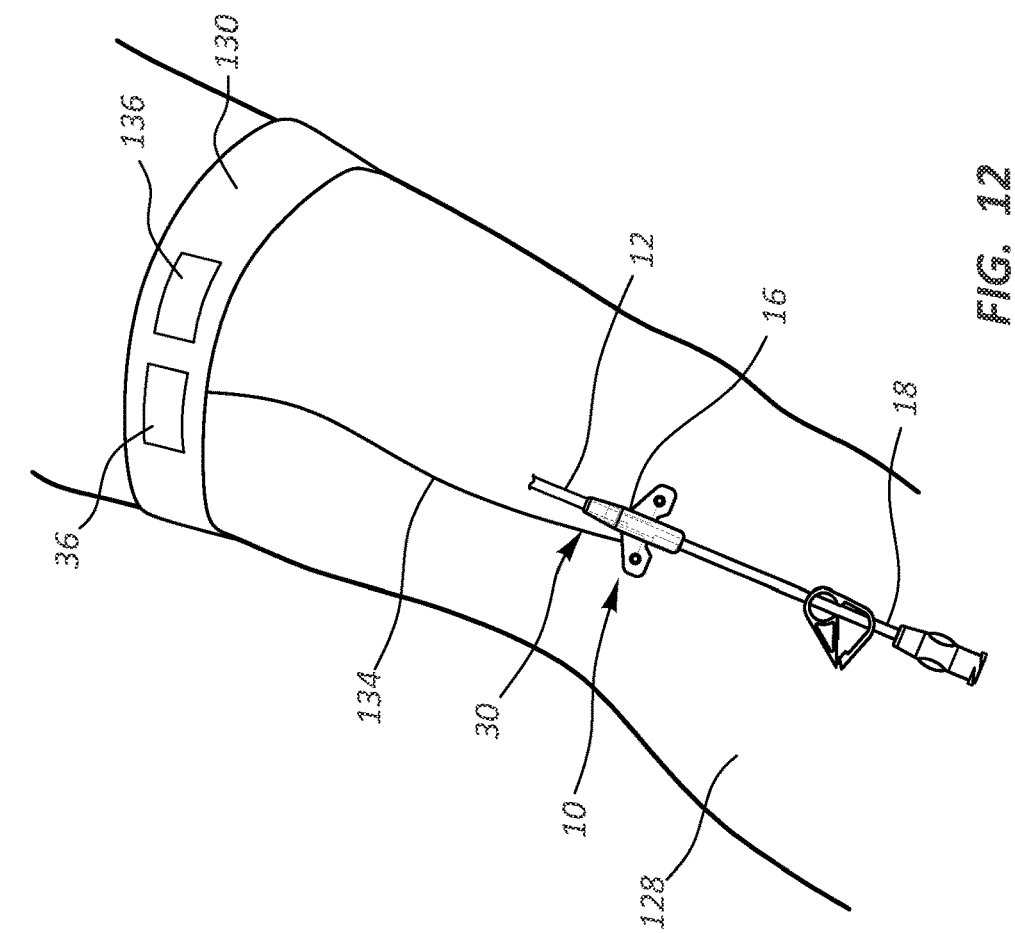

FIG. 12 depicts the catheter 10 in accordance with some embodiments, wherein the catheter is shown inserted into an arm 128 of the patient such that a majority portion of the catheter tube 12 is disposed within the vasculature of the patient. The hub 16, including one or more sensors, is also shown operably connected to an auxiliary device, such as an armband 130, placed around the patient arm 128 via a connecting wire 134. The armband 130 is placed in proximity to the external portion of the catheter 10 in some embodiments, though its location and particular shape, size, configuration, and body attachment scheme can vary in other embodiments. As shown, the armband 130 includes various components to work in concert with the sensor(s) of the catheter 10 via the connection wire 134, including the PCB 36 and a wireless communication module 136 (which in other embodiments is included with the PCB). Sensor data detected by the sensor(s) of the catheter 10 can be forwarded from the catheter 10 to the components of the armband 130 via the connecting wire 134, where the data can be processed (e.g., by the PCB 36) or transmitted to a remote location (e.g., by the wireless communication module 136). In some other embodiments, the operable connection between the catheter 10 and the armband 130 is a wireless connection as well.

Placement of the PCB 36 and the wireless communication module 136 on the armband 130 frees up space on the catheter and may prevent the need for replacing relatively expensive components when the catheter 10 itself is periodically replaced with a new catheter. In such a case, the armband 130 can be simply connected to the new catheter, and the PCB 36 and wireless communication module 136 can begin to function with the new catheter as they did with the previous catheter. Note that various other components can also be included on the armband 130, including a battery for powering the sensor(s) included on the catheter, additional sensors including an ECG sensor, etc. As mentioned, the armband 130 is representative of other wearable and non-wearable auxiliary devices that can be operably connected to the sensor(s) of the catheter 10 in order to facilitate their operation. Also note that the components included on the armband/auxiliary device can be replaceable/reusable. In some embodiments, the PCB, battery, or wireless communication module can be included on the catheter securement device. In some other embodiments, the above-described components can be included on a platform that is removably attachable to the armband. In some other embodiments, the armband or similar component includes a disposable shield to isolate it from the patient or to provide isolation from contaminants.

Figure 13:
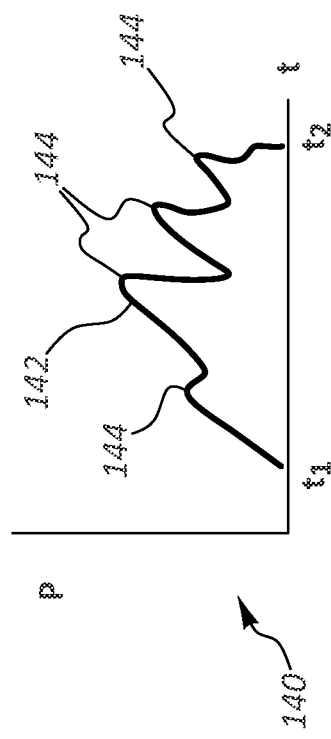

Several of the above-described embodiments include the pressure sensor 32 that is configured to sense data relating to the central venous pressure of the patient in which the catheter 10 is disposed. In some other embodiments, data sensed by the pressure sensor 32 can be further employed to detect when an occlusion, such as a fibrin sheath or thrombus, may be present in the lumen 14 of the catheter tube 12. FIG. 13 shows a pressure graph 140 including a pressure curve 142 that depicts the level of pressure over time in the catheter tube lumen 14 as sensed by the pressure sensor 32, such as in the pressure sensor configuration of FIG. 10, for instance, during a flushing procedure wherein fluid is flushed through the catheter 10 by a user using a syringe connected to the Luer connector 20 in order to maintain patency of the catheter tube lumen 14. As shown, the pressure curve 142 includes various pressure peaks 144 that are caused by the user pulsing the syringe with moments of additional pressure. This is performed so as to clear any minor obstructions that may have formed within the catheter tube lumen 14 or in other areas of the catheter fluid path. When an occlusion is present at the distal end 13 of the catheter tube or within the lumen 14 (see occlusion 178 in FIG. 15 for example), the pressure curve 142 will be elevated (i.e., shifted vertically upward along the pressure y-axis) or widened (i.e., lengthened along the time x-axis).

In more detail, hydraulic resistance R of a fluid is generally related to the fluid flow rate Q and infusion pressure P by the relationship:

$$P=Q*R, \qquad (1)$$

which yields:

$$R=t1 \int t2 P dt/V, \qquad (2)$$

where V is a known volume of fluid to be infused into the catheter 10, t1 is the time at the beginning of a fluid infusion process, t2 is the time at the end of the fluid infusion process (referring to FIG. 13), noting that P indicates the instantaneous pressure during each moment of the fluid infusion procedure. Comparing the resistance R of the fluid infusion through the catheter tube 12 for a certain period of time (using the above equations) and comparing it with the resistance R0 at a previous time, such as when the catheter 10 was first inserted into the patient and was considered un-occluded, or patent, can yield the percentage of possible occlusion in the catheter tube according to:

$$\% \text{ occlusion}=R/R0 \qquad (3)$$

Detection of an elevated pressure within the catheter fluid path by the pressure sensor 32, such as via the above-described calculations, can alert the user to a possible occlusion such that corrective measures can be taken. Further, data storage in a memory location located on the catheter 10 with the PCB 36 or remotely located in a patient electronic medical record (or other remote storage location) can be employed to measure the catheter flushing pressure over time so as to detect pressure changes over time. This data comparison over time can be performed for any one of the sensors located on the catheter 10, as may be appreciated. Of course, the data sensed by the sensors and stored in a memory location can be used for a variety of other uses as well, including historical trends, etc.

Figure 14:
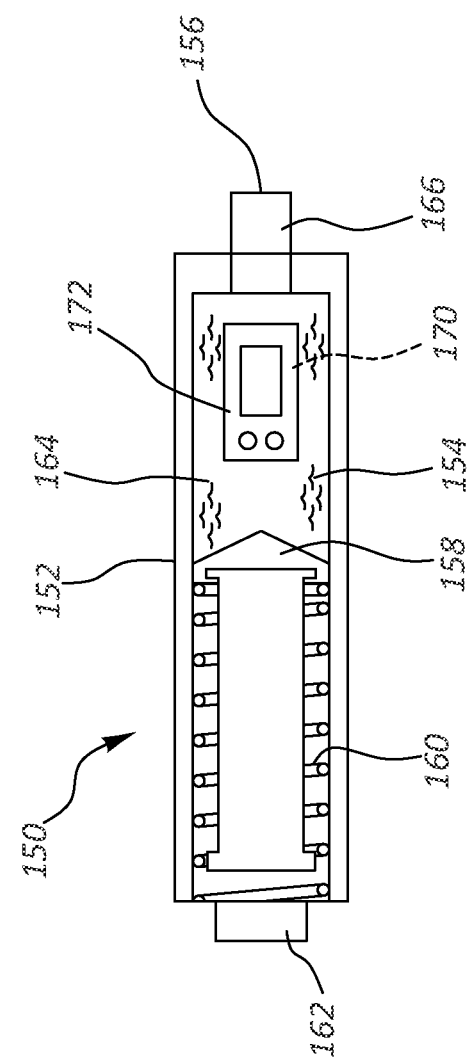

FIG. 14 depicts various details of a pressure-sensing syringe 150 including a housing 152 that defines a cavity 154 with a distal end fluid outlet 156. A plunger 158 is disposed within the cavity 154 and is attached to a spring 160, initially disposed in a compressed state and releasable by a release button 162 disposed on a proximal end of the syringe 150. A known quantity of 0.9% normal saline 164 or other suitable liquid is disposed in the cavity distal to the plunger 158 such that the saline exits the fluid outlet 156 when the spring 160 is actuated by the release button 162. The saline 164 ejected by the syringe 150 is injected into the extension leg 18—then through the hub 16 and lumen 14 of the catheter tube—when the syringe is operably attached to the corresponding Luer connector 20.

A pressure sensor 166 is included at the fluid outlet 156 to measure the pressure of the known quantity of saline 164 as it exits the fluid outlet 156 and enters the catheter 10 to which the syringe 150 is connected. A processor unit 170 and a display/control unit 172 are included to measure and calculate (such as via the equations described further above) the pressure present as the saline 164 is ejected by the plunger 158 through the fluid outlet 156. Further calculations can be performed by the processor unit 170 to determine the hydraulic resistance of the injection, thus yielding the amount of occlusion present in the fluid path of the catheter 10, using the known volume of injected saline 164, the injection pressure as measured by the pressure sensor 166, and the amount of time needed for injection of all the saline to occur. In some embodiments, the user can input the size of the catheter tube lumen 14 and the length thereof via the display/control unit 172.

The results describing the amount of any occlusion present in the catheter fluid path (such as in % of fluid path occluded, for instance) can be depicted on the display/control unit 172 or wirelessly transmitted to a receipt location via a wireless communication module included with the processor unit 170, for instance. Corrective measured can then be taken by the user, if needed.

Note that historical pressure/occlusion data can be stored by a memory location of the processor unit 170, for instance, for call-up and depiction by the display/control unit 172. In some embodiments, the plunger 158 of the syringe 150 is manually depressible by the user, thus obviating the need for the spring 160, or can be a pressurized gas source to push the plunger, etc. The location of the pressure sensor 166 can also vary from what is shown and described herein.

Note that, in some other embodiments, the pressure sensor 32 can be used to determine when the catheter tube 12 has been malpositioned within the vasculature by sensing pressure differences between expected values for a proper placement and actual sensed values as detected by the pressure sensor. When this situation occurs, proper steps to correct the malposition can be taken. In some other embodiments, the pressure sensor 32 and the electrical (ECG) sensor 34 can work in concert to detect catheter malposition based on venous pressure readings and ECG signal analysis.

Figure 15:
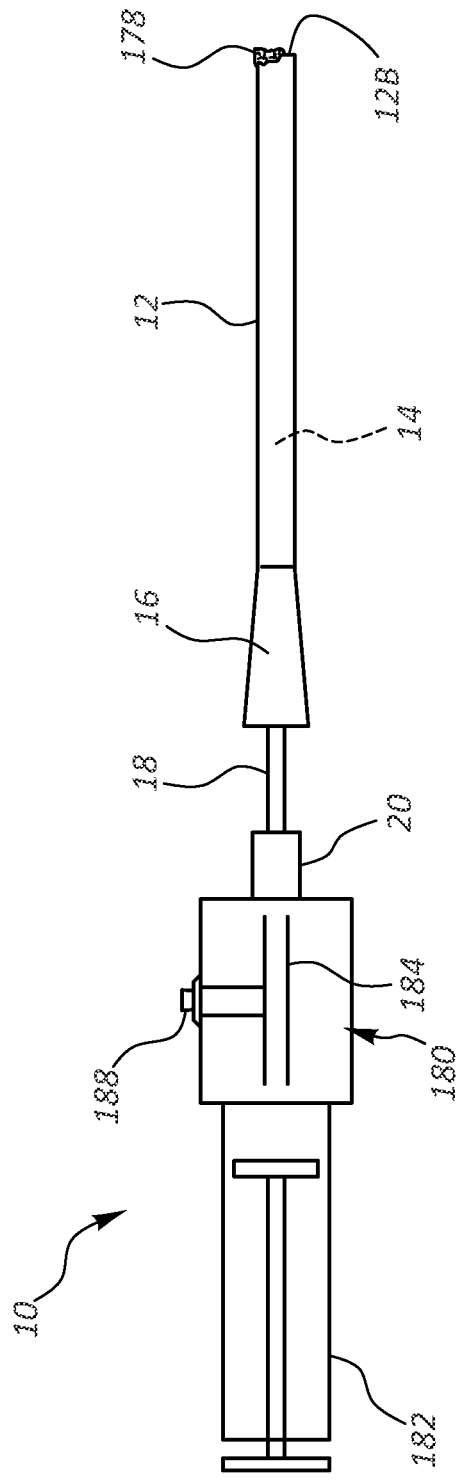

FIG. 15 depicts various details of the catheter 10 that includes the ability to detect occlusions, such as a partial occlusion 178 shown at the distal end 13 of the catheter tube 12. As shown, the catheter 10 includes a pressure detection module 180 operably attached to the Luer connector 20 of the catheter 10. A syringe 182 is attached to a proximal end of the pressure detection module 180 so as to provide an injection of saline or other suitable fluid through a flow lumen 184 of the pressure detection module 180 and into the extension leg 18 to flow through the catheter 10.

As shown, the pressure detection module 180 includes a pressure indicator 188 in fluid communication with the flow lumen 184. The pressure indicator 188 is configured to extend an indicator piece outward when a predetermined pressure is encountered in the flow lumen 184 of the pressure detection module. As such, when a fluid pressure in excess of the predetermined pressure is encountered in the catheter lumen 14 during fluid injection into the system by the syringe 182 (or other suitable fluid injection device), the pressure buildup extends proximally through the hub 16, extension leg 18, and flow lumen 184, causing the indicator piece of the pressure indicator to extend outward, thus indicating to the user that an occlusion may be present. It is appreciated that indicator pieces of differing configurations can be employed. The pressure detection module 180 can be a separate component attachable to the catheter 10; in some other embodiments, the pressure detection module is integrally formed with the catheter.

Figure 16:
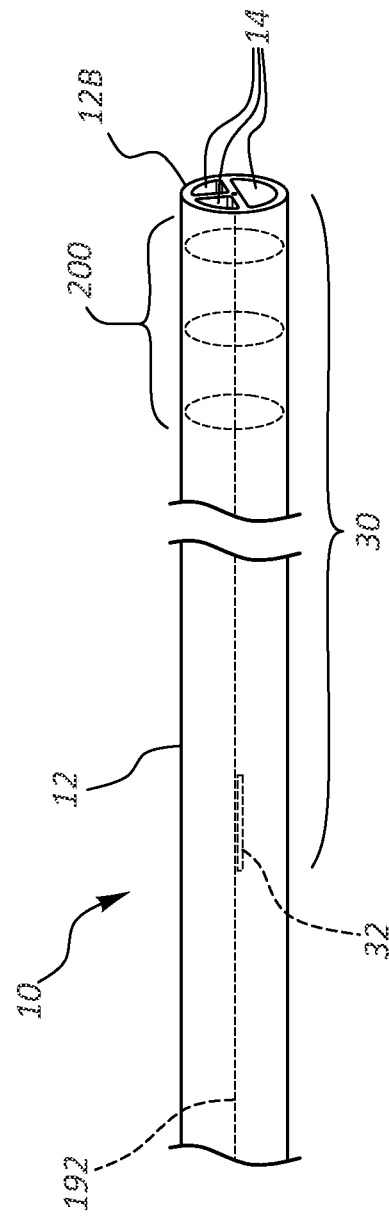

FIG. 16 depicts possible locations for sensors of the sensor array 30 in the catheter tube 12. As shown, various sensors 200 of the sensor array 30 are disposed proximate the distal end 13 of the catheter tube 12, together with the pressure sensor 32 disposed proximally to the other sensors. FIG. 16 further shows that a connection wire 192 extends along a central portion of the catheter tube, e.g., within a septum separating the lumens 14 from one another, to power the sensors 200 of the sensor array 30. In some other embodiments, the connection wire 192 can be disposed in a dedicated lumen extending the length of the catheter tube. Note that placement of the sensor(s) a distance proximal to the catheter tube distal end 13, such as the pressure sensor 32 here, enables the catheter tube 12 to be distally trimmable.

Figure 17:
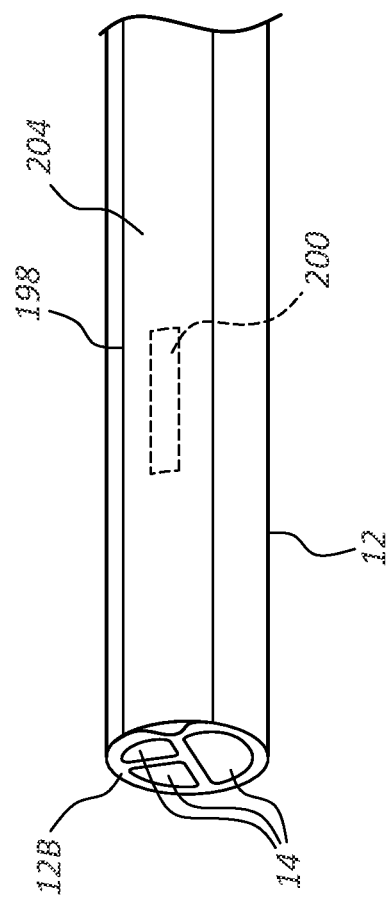

FIG. 17 depicts another configuration for including a sensor 202 in the catheter tube 12, wherein the sensor 202 is disposed in the wall of the catheter tube 12 within a skive cut 198 longitudinally defined in the wall. Potting 204, such as a thermally conductive epoxy, polyurethane, or RTV potting, is included to cover the sensor 202. In some embodiments, the sensor 202 includes a glucose sensor for sensing blood glucose levels and is not potted such that the glucose sensor has direct contact with the blood. These and other possible sensor locations are therefore contemplated.

Figure 18:
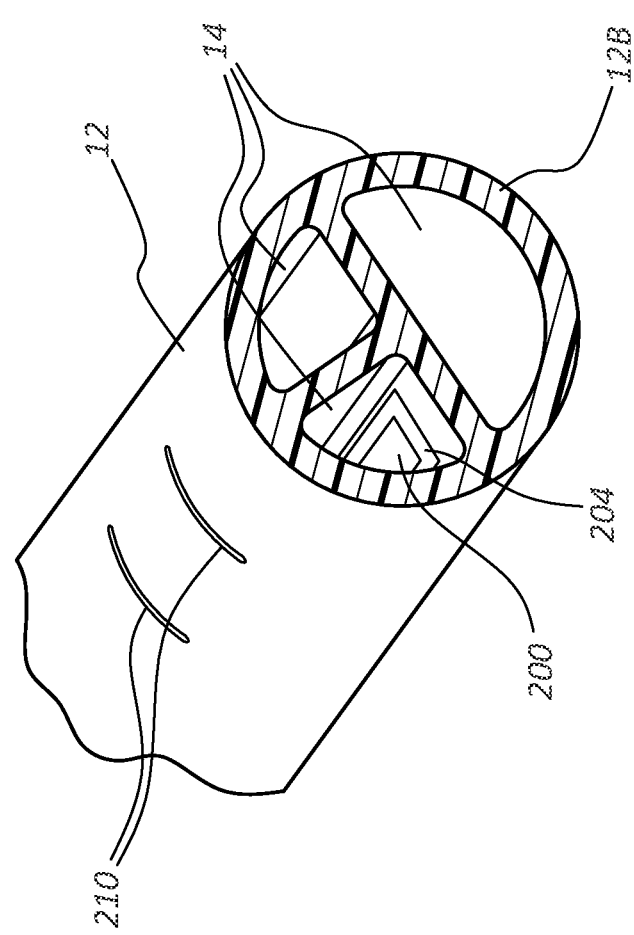

FIG. 18 depicts another configuration for including a sensor in the catheter tube 12, wherein the sensor 202 is disposed on an inner surface of one of the lumens 14 of the catheter tube 12 proximate the distal end 13 of the catheter tube 12 or within a septum dividing the luminal space within the catheter tube 12 into two or more lumens 14. Potting 204 can be included to insulate and cover the sensor 202 as needed. In some embodiments, the potting 204 protects the sensor 202 from exposure to liquids while enabling heat to be transmitted therethrough. FIG. 18 further shows that wire-based electrodes 210 can be disposed in the wall of the catheter tube 12 proximate the distal end 13 of the catheter tube 12 so as to be exposed on an outer surface thereof. The electrodes 210 can be formed as concentrically disposed sensors that can be employed to make volumetric measurements to determine the size of the vessel in which the catheter tube is disposed, thus assisting the user in determining a possible malposition of the catheter tube in an undesired vessel. These and other possible sensor configurations are therefore contemplated.

FIG. 19 depicts various details of a flush sensor 222 for detecting when the desired periodic flushing of the catheter 10 with a fluid has occurred, also referred to herein as a flush state of the catheter tube 12. As shown, the flush sensor 222 is disposed within a cavity 220 of the Luer connector 20 of the catheter extension leg 18, though other locations can be employed for the sensor such as within the hub 16, wherein the flush sensor 222 is optionally a thermistor. The flush sensor 222, also referred to herein as a detection module, includes a lever 224 biased to an extended position by a spring 226, as shown. The flush sensor 222 is operably connected to a processor of a PCB (such as the PCB 36 shown in FIG. 10) or other suitable component (disposed within the Luer connector 20, for instance) to govern its operation and process its sensed data.

In operation, when a syringe or other component is inserted into the cavity 220 of the Luer connector 20 to flush the catheter 10 with saline or other suitable fluid, the lever 224 of the flush sensor 222 is depressed, which causes a signal to be sent to the processor indicating that a flushing procedure is occurring. The time of flushing or other data relating to the flushing procedure can be noted, stored or used by the processor, or wirelessly transmitted to a receipt location in a manner similar to that discussed further above. In some embodiments, the flush sensor 222 and the processor of the PCB 36 are referred to as a flush sensor assembly, though it is appreciated that the assembly can include additional components. In some other embodiments, an electrical sensor can be employed as the flush sensor, wherein the electrical sensor includes a circuit that is broken each time a component is inserted into the connector 20. Breaking of the circuit can reset a timer circuit to measure the next period until the flush sensor is again activated.

In some embodiments, for instance, it is desired that the catheter 10 be flushed at least once every 12 hours. When the flush sensor 222 detects a flushing procedure as described above, a timer circuit in the processor is re-set to begin counting time to measure the next time period until the flush sensor 222 is again depressed to indicate a new flushing procedure.

FIG. 20 shows that a light array 230, such as a collection of a red LED light, yellow LED light, and green LED light, can be included on a surface of the Luer connector 20 to visually indicate the flushing status of the catheter 10: a green light indicates less than 10 hours have elapsed since the last flushing procedure was detected; a yellow light indicates more than 10 hours but less than 12 hours have elapsed since the last flushing procedure; a red light indicates that more than 12 hours have elapsed since the last flushing procedure. The processor governs the operation of the light array and it is understood that the lights can vary in number size, location, purpose, indicated elapsed time, etc. Further, it is appreciated that other types of sensors, including sensors that detect the presence of liquid within the Luer connector cavity 220, can also be employed to detect flushing procedures.

In some other embodiments, the light array 230 can be used as follows: the green light flashes after an acceptable flushing procedure has been performed; the red light blinks after a non-acceptable or incomplete flushing procedure has occurred; the yellow light blinks or is turned on to indicate a possible occlusion present in the catheter tube 12. In some other embodiments, the yellow light (or other light) can be lit to serve as a reminder to flush the catheter 10.

It is appreciated that in some other embodiments, the Luer connector 20 or other portion of the catheter 10 can include a push button (or other user-activated component) that can be depressed at the time of catheter flushing, thus re-setting the timer circuit. In this case, a counting circuit can also be included to count the number of times the connector 20 or other component is accessed.

FIG. 21 shows that the light array 230 can be disposed in other locations on the catheter 10, including disposal on the hub 16. These and other possible locations, such as the catheter tube or extension legs, or the armband 130 of FIG. 12 for example, are therefore contemplated. In some other embodiments, the light array can be employed to alert the user to other sensed conditions, including elevated body temperature/fever, onset of sepsis (see further below), catheter occlusion, low blood oxygen levels, etc. Further, other indicia can be employed, in addition to lights, to alert the user with respect to the sensor data, including sound, vibration, etc. either on the catheter itself or at the remote receipt location to where the data is wirelessly transmitted.

Note that the flush sensor 222 can be included in other areas as well, including a needleless connector that is configured to operably attach to the Luer connector, for instance.

In some embodiments, the pressure sensor 32 can be used—alone or in concert with the flush sensor 222 described above—to detect or characterize flushing procedures. For instance, the flush sensor 222 can be used to detect a flushing procedure, while the pressure sensor 32 can sense the amount of pressure present during the flushing procedure, thus detecting possible occlusions. Indeed, in some embodiments, the pressure sensor 32 can be used to determine flushing frequency of the catheter 10, flushing technique, flushing time, number of times of catheter access, time expired since last catheter access, etc., by measuring pressure within the lumen 14 of the catheter as a function of time, using timer circuitry included on the PCB 36, for instance. Such sensor data can be stored by a memory location located on the PCB 36, for instance, or transmitted to another local or remote receipt location, as has been described. Processing to determine such monitoring can be performed by a processor included on the PCB 36 or remotely.

In some embodiments, sensor data from catheter sensors, such as the pressure sensor 32 and a core body temperature sensor, can be employed to detect patient conditions, such as sepsis. In particular, blood flowrate, respiratory rate, heart rate, and body temperature can be sensed via the pressure sensor 32 and the core body temperature sensor 100 included with the catheter 10, such as in the configuration shown in FIG. 10. These three parameters comprise three of four parameters that are typically employed to determine the onset of sepsis. As such, monitoring of these parameters via the catheter 10 as described herein can be used to prevent detect and ameliorate complications from sepsis.

Figure 22:
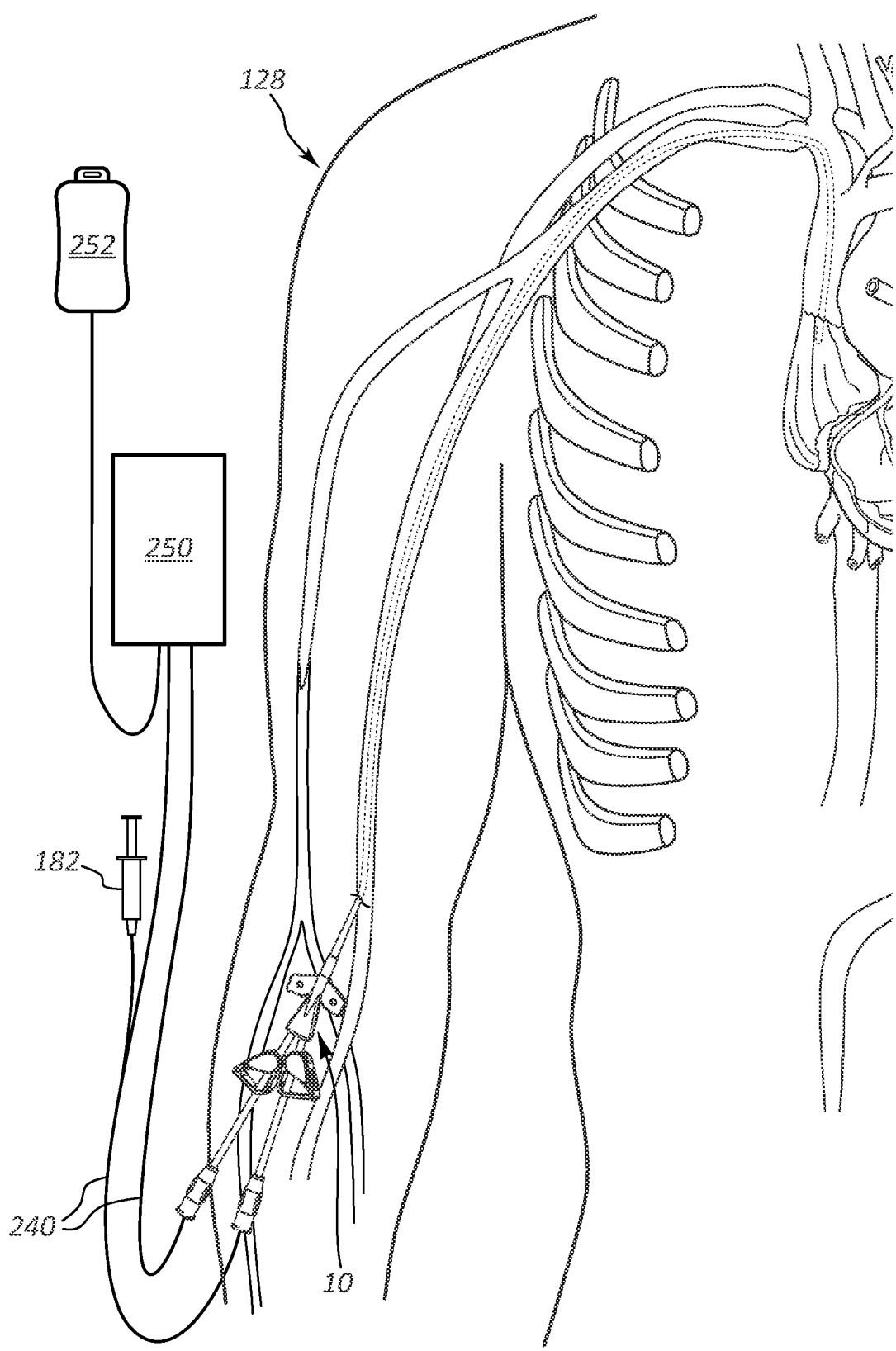

FIG. 22 depicts a sensor-based catheter assembly in accordance with some embodiments. In detail, the catheter 10 is shown with its catheter tube 12 disposed within the vasculature of the patient and the two Luer connectors 20 operably connected to supply lines 240 configured to both provide fluid to and remove fluid from the lumens of the catheter. A pump unit 250 is included to enable fluid movement through the supply lines 240. A saline fluid drip assembly 252 is also included to provide fluid to the pump unit for movement through the supply lines, if needed or desired. A syringe, such as the syringe 182, is included to provide an additional fluid inlet in a corresponding one of the supply lines 240.

Figure 23:
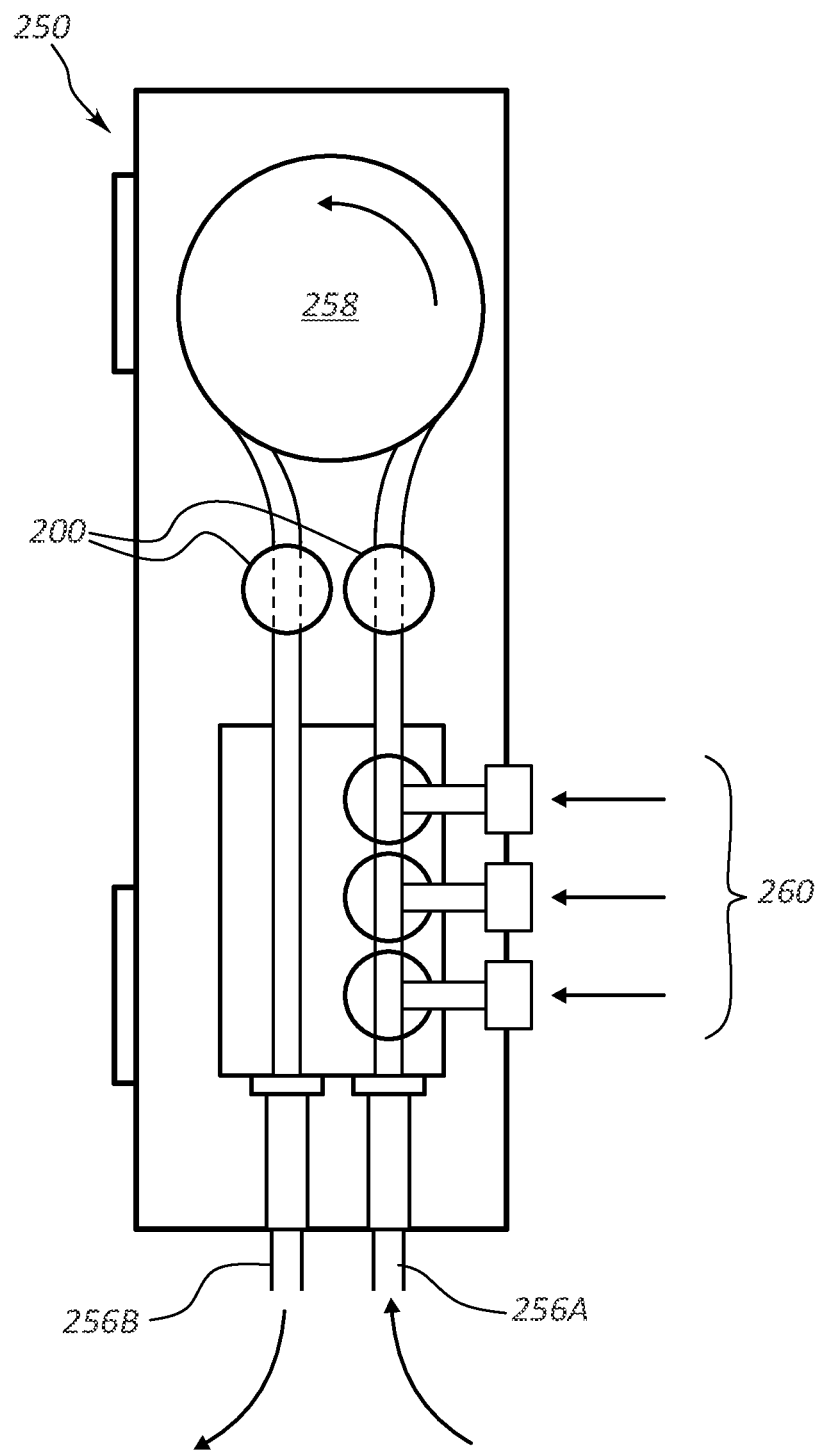

FIG. 23 depicts further details of the pump unit 250 of FIG. 22, including a fluid inlet 256A and a fluid outlet 256B that are configured to operably connect with the corresponding supply lines 240 (FIG. 22) to bring blood or other fluid from within the patient vasculature via the catheter 10 (through the fluid inlet 256A) to the pump unit 250 and to return the fluid to the patient vasculature (through the fluid outlet 256B) via the catheter. A pump 258 is included in the pump unit 250 to cause the movement of the fluid. Additionally, various input ports 260 are included on the pump unit 250 in fluid communication with the fluid inlet 256A to enable additional fluids to be input, including heparin, saline, arterial input, etc.

One or more sensors 262 are also included in the pump unit 250 and arranged so as to measure one or more physiological aspects of the patient blood. Examples of such sensors include a glucose meter, oxygen sensor, lactic acid sensor, cardiac output sensor, etc. The location of the sensors 262 can vary from what is shown here. Disposal of the sensors 262 in the pump unit 250 as opposed to the on the catheter 10 itself enables sensors of relatively greater size to be employed without unduly increasing the size of the catheter.

Diagnostic Systems

Figure 24:
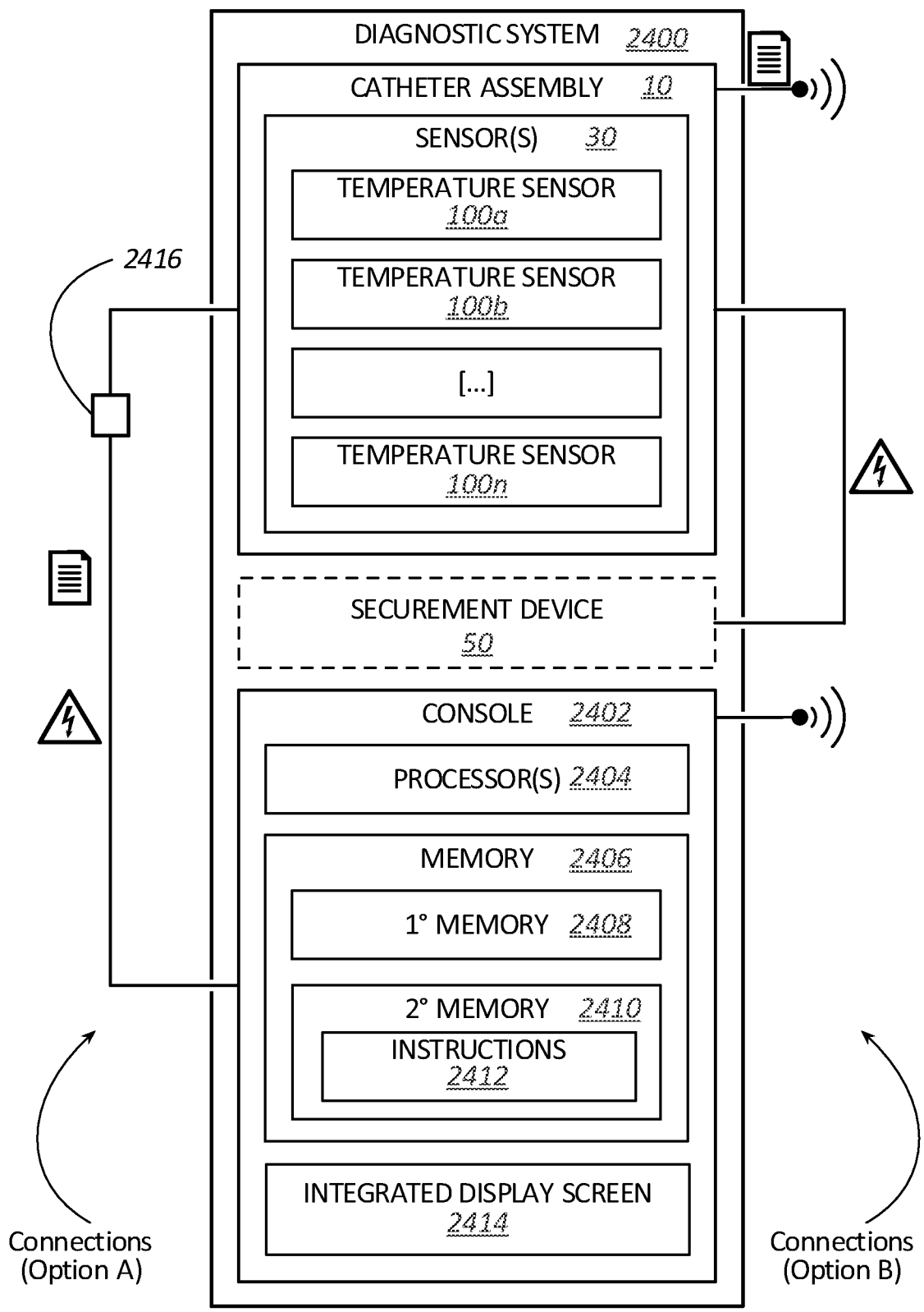
Figure 25:
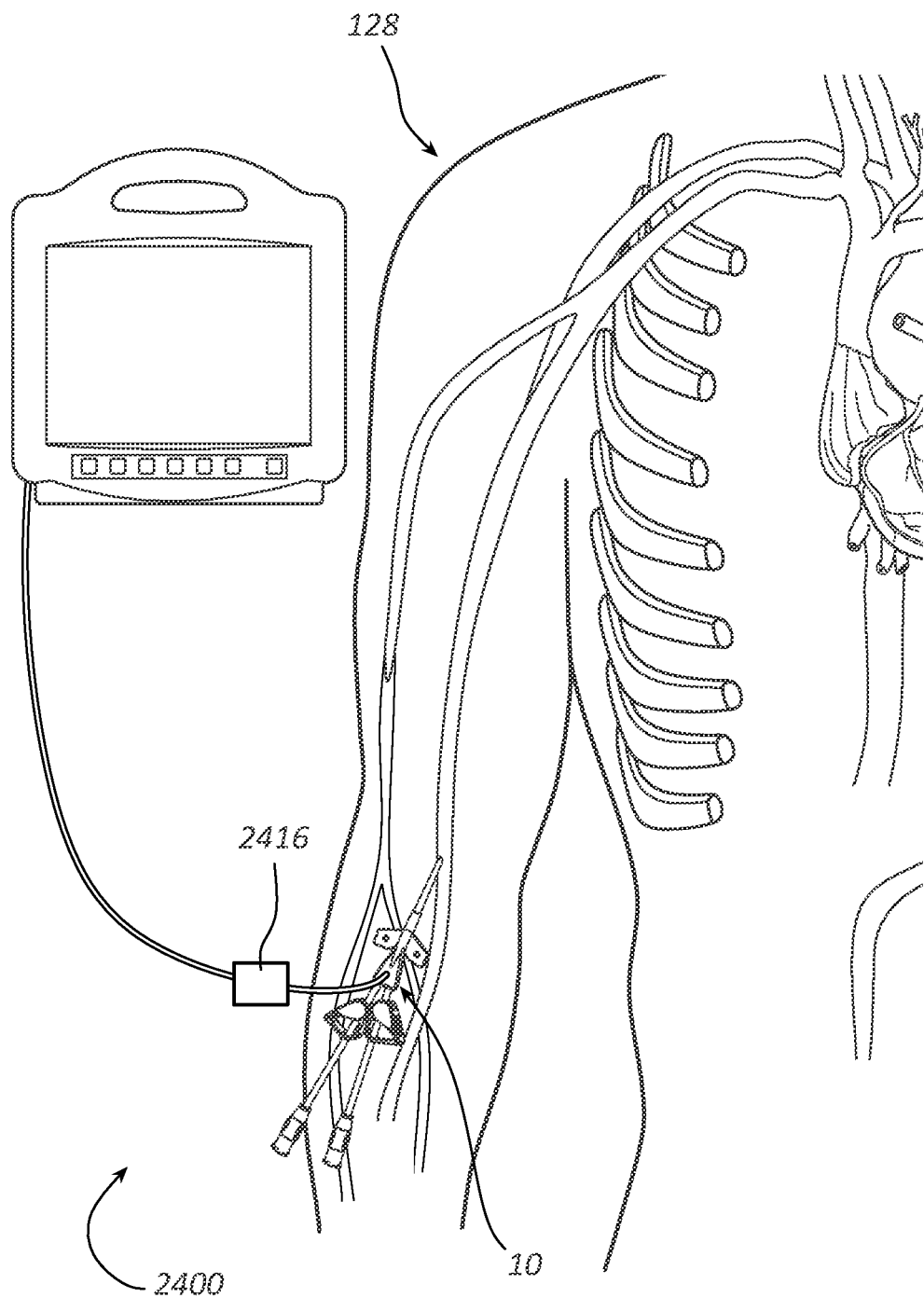
FIG. 25 illustrates the diagnostic system configured for wired communication in use on a patient in accordance with some embodiments.
Figure 26:
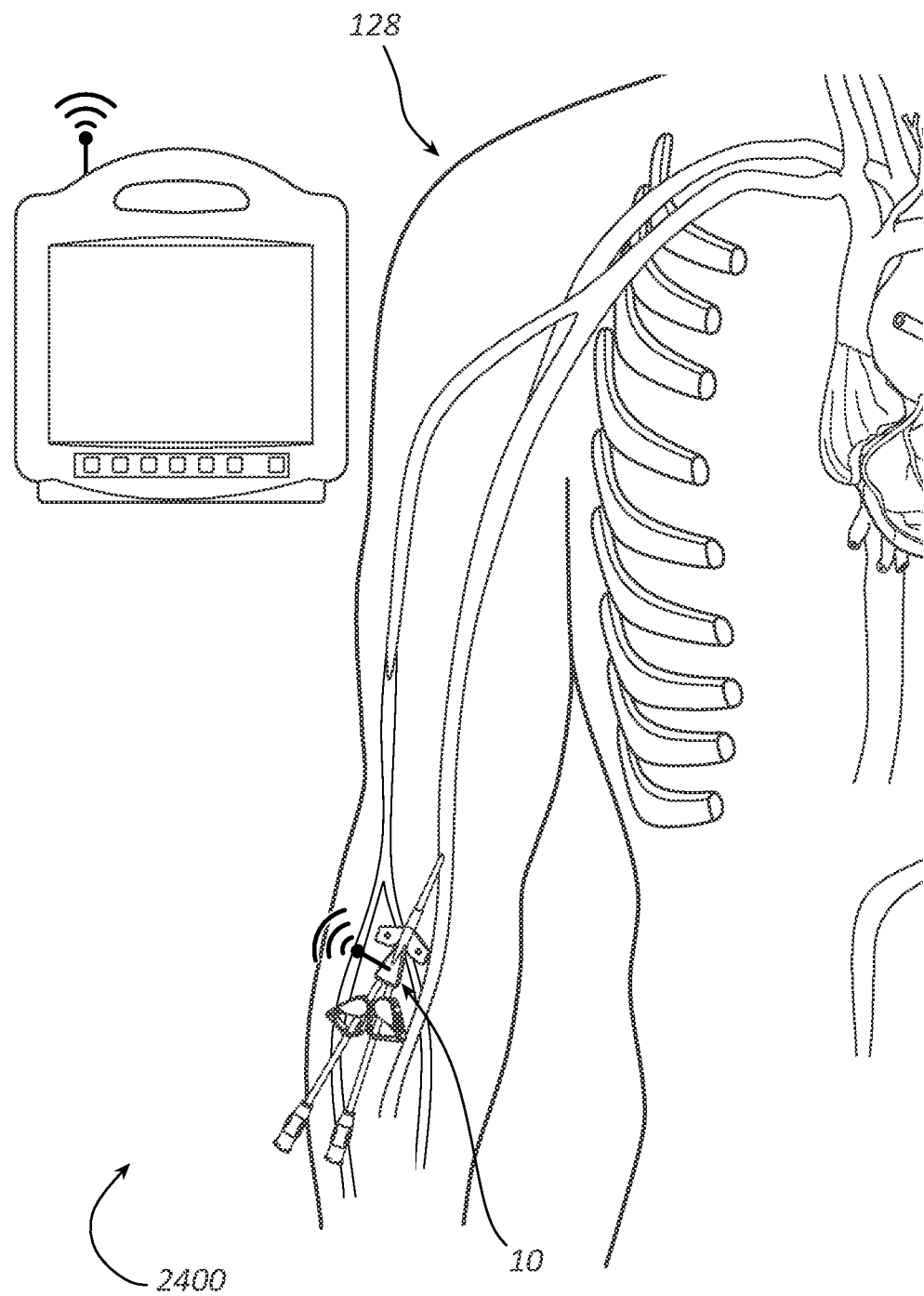
FIG. 26 illustrates the diagnostic system configured for wireless communication in use on a patient in accordance with some embodiments.

FIG. 24 provides a block diagram of a diagnostic system 2400 including the catheter assembly 10 and a console 2402 configured for either wired or wireless communication in accordance with some embodiments. FIGS. 25 and 26 illustrate the diagnostic system 2400 in use on a patient in accordance with some embodiments, wherein the diagnostic system of FIG. 25 is configured for wired communication and the diagnostic system of FIG. 26 is configured for wireless communication.

As shown, the diagnostic system 2400 includes the catheter assembly 10, the console 2402, and a display screen 2414, of which the catheter assembly 10 is single-use disposable equipment while the console 2402 and display screen 2414 are multi-use capital equipment. While the display screen 2414 can be an integrated display screen integrated into the console 2402 as shown, the display screen 2414 can alternatively be a separate display screen of a monitor compatible with the diagnostic system 2400 or the console 2402 thereof. Regardless, the display screen 2414 is configured to communicate with the console 2402 and display thereon a GUI including at least a temperature reading associated with the one or more sensors 30 of the catheter assembly 10 while the catheter tube 12 is disposed in a vasculature of a patient.

It should be understood that the catheter assembly 10 is an example of a vascular access device that can be used in the diagnostic system 2400 with the console 2402 and the display screen 2414. Indeed, the vascular access device can instead be a cannula or a needle. As such, disclosure with respect to the catheter assembly 10 should be understood to include other vascular access device such as the foregoing cannula or needle except when the disclosure is exclusively directed to features of the catheter assembly 10.

As set forth above, the catheter assembly 10 includes the catheter tube 12, the hub 16 operably attached to the catheter tube 12, one or more extension legs 18 operably attached to the hub 16 commensurate with a number of lumens or fluid passageways of the catheter assembly 10, and the one or more sensors 30 such as a single temperature sensor (e.g., the temperature sensor 100 in FIG. 9A or 9B) or a plurality of temperature sensors (e.g., a temperature sensor $100a$, a temperature sensor $100b$, ..., a temperature sensor $100n$ as shown in FIG. 24).

If the vascular access device is a cannula or a needle, the cannular or needle can include the foregoing one or more sensors 30. For example, such a vascular access device can have a single temperature sensor disposed within a distal-end portion of an elongate tube thereof configured for temperature measurement therein when disposed in a vasculature of a patient.

The catheter tube 12 defines at least one lumen extending between a proximal end and a distal end 13 of the catheter tube 12 as shown in FIG. 1. Together with at least one lumen of the hub 16 and at least one lumen of an extension leg 18, the at least one lumen of the catheter tube 12 defines at least one fluid passageway through the catheter assembly 12. The catheter assembly 10 can be a monoluminal catheter assembly 10 such as the monoluminal catheter assembly 10 of FIG. 1 having only the foregoing fluid passageway. Alternatively, the catheter assembly 10 can be a multiluminal catheter assembly such as the diluminal catheter assembly 10 of FIG. 2 having two fluid passageways through the catheter assembly 10 or the triluminal catheter assembly 10 of FIG. 3 having three fluid passageways through the catheter assembly 10.

The one or more sensors 30 can include the single temperature sensor (e.g., the temperature sensor 100 in FIG. 9A or 9B) or the plurality of temperature sensors (e.g., a temperature sensor $100a$, a temperature sensor $100b$, ..., a temperature sensor $100n$ as shown in FIG. 24).

When the catheter assembly 10 has the single temperature sensor 100, the single temperature sensor 100 can be disposed within the catheter tube 12, the hub 16, or the extension leg 18 for temperature measurement therein. For example, as set forth above with respect to the catheter assembly 10 of FIG. 9A, 9B, or 17, the single temperature sensor 100 can be disposed within a wall of catheter tube 12. Alternatively, the single temperature sensor 100 can be disposed on or within a septum of the catheter tube 12 as set forth above with respect to the catheter assembly 10 of FIG. 18. Electrical leads for connecting the single temperature sensor 100 to an electrical power source such as the securement device 50 or the console 2402 can be disposed in the wall of catheter tube 12, a septum of the catheter tube 12, or both the wall of the catheter tube 12 and a septum of the catheter tube 12 as needed.

When the catheter assembly 10 has the plurality of temperature sensors 100a, 100b, ..., 100n, the plurality of temperature sensors 100a, 100b, ..., 100n can be disposed within the catheter tube 12, the hub 16, the extension leg 18, or a combination thereof configured for temperature measurement therein. For example, the catheter tube 12 can include at least one temperature sensor disposed within the catheter tube 12 for temperature measurement in the catheter tube 12, the hub 16 can include at least one temperature sensor disposed within the hub 16 for temperature measurement in the hub 16, or each component of the catheter assembly 50 of the catheter tube 12 and the hub 16 can include at least one temperature sensor disposed therein for temperature measurement.

As set forth above with respect to the catheter assembly 10 of FIG. 9A, 9B, or 17, a temperature sensor such as any temperature sensor of the plurality of temperature sensors 100a, 100b, ..., 100n can be disposed within a wall of catheter tube 12. Alternatively, a temperature sensor such as any temperature sensor of the plurality of temperature sensors 100a, 100b, ..., 100n can be disposed on or within a septum of the catheter tube 12 as set forth above with respect to the catheter assembly 10 of FIG. 18. A combination of the plurality of temperature sensors 100a, 100b, ..., 100n within the wall of the catheter tube 12 and one or more septa of the catheter tube 12 is also possible. Whether the plurality of temperature sensors 100a, 100b, ..., 100n are disposed within the wall of the catheter tube 12, on or within a septum of the catheter tube 12, or a combination thereof, the plurality of temperature sensors 100a, 100b, ..., 100n can be disposed intermittently along the length of the catheter tube 12. Having each temperature sensor of the plurality of temperature sensors 100a, 100b, ..., 100n disposed in a different location of a plurality of locations along the length of the catheter tube 12 is useful for measuring local temperatures at the different locations. Electrical leads for connecting the plurality of temperature sensors 100a, 100b, ..., 100n to an electrical power source such as the securement device 50 or the console 2402 can be disposed in the wall of catheter tube 12, a septum of the catheter tube 12, or both the wall of the catheter tube 12 and a septum of the catheter tube 12 as needed.

The console 2402 includes memory 2406 such as primary memory 2408 and secondary memory 2410. The primary memory 2408 includes random-access memory ("RAM"). The secondary memory 2410 includes non-volatile memory such as read-only memory ("ROM") having instructions 2412 for loading into the primary memory 2408 at runtime of the console 2402 for instantiating a diagnostic process of the console 2402 having one or functions for at least processing temperature data from the one or more sensors 30 while the catheter tube 12 is disposed in a vasculature of a patient. (See FIGS. 25 and 26 for an example of the catheter tube 12 disposed in the vasculature of the patient.) The instructions 2412 can include those for the diagnostic process, one or more functions of the diagnostic process, one or more algorithms for processing the temperature data, or a combination thereof. The instructions 2412 can also be for instantiating a display server configured to coordinate input to the console 2402 and output from the console 2402. The input to the console 2402 includes selection of the one or more functions of the diagnostic process such as through the GUI on the display screen 2414. The output of the console 2402 includes the GUI on the display screen 2414.

The console 2402 is configured to communicate with both the catheter assembly 10 and the display screen 2414, as well as power the catheter assembly 10 when the securement device 50 is not used. Such communication and power options are shown among FIGS. 24-26. For example, the catheter assembly 10 can have a wired connection to the console 2402 through a connector 2416, wherein the wired connection permits power to be provided to the catheter assembly 10 from the console 2402 and data (e.g., the temperature data) to be provided to the console 2402 from the catheter assembly 10. (See FIG. 24, Connections, Option A.) In another example, the catheter assembly 10 can have a wireless communication module configured to provide data (e.g., the temperature data) to a wireless communication module of the console 2402. Again, in embodiments in which wireless communication is used to transfer data, power to the catheter assembly 10 can be provided by the securement device 50. (See FIG. 24, Connections, Option B.)

The one or more algorithms for processing the temperature data are useful for processing the temperature data from any temperature sensor of the catheter assembly 50 with the diagnostic process while the catheter tube 12 is disposed in a vasculature of a patient. For example, the one or more temperature data-processing algorithms can include an infection-diagnosis algorithm for diagnosing infection in the vasculature or subcutaneous tissue of the patient. (Other temperature data-processing algorithms are set forth below with respect to certain functions of the diagnostic process.) When the catheter assembly 50 includes the plurality of temperature sensors 100a, 100b, ..., 100n disposed in the plurality of locations along the length of the catheter tube 12, the infection-diagnosis algorithm can be used by the diagnostic process for diagnosing infection in the vasculature of the patient at any one or more locations of the plurality of the locations along the length of the catheter tube 12. Diagnosing infection with the infection-diagnosis algorithm is in accordance with local temperature changes or trends thereof sensed by the temperature sensor or the temperature sensors respectively at the one or more locations of the plurality of the locations. For example, an infection can be diagnosed at an insertion site by an increasing trend in temperature among the temperature data provided by a temperature sensor at the proximal end of the catheter tube 12. In another example, sepsis can be diagnosed by an increasing trend in temperature among the temperature data provided by several temperature sensors of the plurality of temperature sensors 100a, 100b, ..., 100n along the length of the catheter tube 12.

The one or more functions of the diagnostic process can include a flushing-compliance function to ensure flushing compliance after blood is drawn from the catheter assembly 50, which, in turn, ensures patency of the catheter assembly 50. The flushing-compliance function is configured to provide an alert such as a visual alert on the console 2402 or the display screen 2414 or an audible alert by the console 2402 when a flushing-compliant temperature change does not occur as expected due to drawing patient-temperature blood drawn from the catheter assembly 50 followed by flushing the catheter assembly 50 with room-temperature flushate or per recommended intervals (e.g., every 12 hours) for flushing the catheter assembly 50 to maintain device patency. As set forth above, the catheter assembly 50 can include at least one temperature sensor disposed within the catheter tube 12 for temperature measurement in the catheter tube 12, at least one temperature sensor disposed within the hub 16 for temperature measurement in the hub 16, or at least one temperature sensor disposed in each component of the catheter tube 12 and the hub 16 for temperature measurement therein. The flushing-compliance function is configured to provide the alert when the flushing-compliant temperature change does not occur at the temperature sensor of the catheter tube 12, the temperature sensor of the hub 16, or both temperature sensors as expected from room-temperature flushate being flushed through the catheter assembly 50, for instance, after patient-temperature blood is drawn from the catheter assembly 50.

The one or more functions of the diagnostic process can include a blood-flowrate function. In accordance with the blood-flowrate function, the diagnostic process utilizes a blood-flowrate algorithm to monitor blood flowrate about a particular or primary temperature sensor disposed in a distal-end portion of the catheter tube 12 or some other length of the catheter tube 12. The primary temperature sensor is communicatively coupled to a PID controller of the console 2402, which PID controller is configured to maintain the primary temperature sensor at a set number of degrees above blood temperature by issuing control signals thereto. The amount of power required to maintain the primary temperature sensor at the set number of degrees above blood temperature is monitored by the blood-flowrate algorithm, for example, by the control signals issued by the PID controller. Because the amount of power required to maintain the primary temperature sensor at the set number of degrees above blood temperature is proportional to the blood flowrate, the diagnostic process can utilize the blood-flowrate algorithm to determine blood flowrate about the primary sensor. Blood flowrate can be used to confirm initial placement of the catheter tube 12 (or the like) into a blood vessel, adequate infusate dilution at the distal end 13 of the catheter tube 12. The blood flowrate can also be used to detect catheter migration or blood vessel occlusions. In addition, the blood flowrate can be used to diagnose an infection at an insertion site, optionally, in conjunction with the infection-diagnosis algorithm. Because a reduction in blood flowrate at an insertion site is often due to swelling from an infection, a measured reduction in blood flow rate by way of the blood-flowrate algorithm can serve as an indicator of the infection or a check on a diagnosis of the infection by way of the infection-diagnosis algorithm.

When the vascular access device is a cannula or a needle and the single temperature sensor in the distal-end portion of the elongate tube thereof is the primary temperature sensor, input to the console 2402 includes a local maximum from blood-flowrate data resulting from the blood-flowrate algorithm and output from the console 2402 to the GUI includes an indication of successful placement of the distal-end portion of the elongate tube in the vasculature of the patient on the display screen 2414.

The one or more functions of the diagnostic process can include a cardiac-parameter function. In accordance with the cardiac-parameter function, the diagnostic process utilizes the blood-flowrate algorithm in combination with a cardiac-parameter algorithm to determine cardiac parameters including heart rate and cardiac stroke volume. The heart rate can be measured through blood flow fluctuations or input from another sensor other than a temperature sensor. For example, the heart rate can be measured through an ECG stylet or the ECG sensor 34.

The one or more functions of the diagnostic process can include a catheter-tracking function. In accordance with the catheter-tracking function, the diagnostic process utilizes the blood-flowrate algorithm in combination with a catheter-tracking algorithm to determine when the primary temperature sensor is advanced past a vascular junction in accordance with a volumetric increase in blood flow. The blood flow and changes in the blood flow resulting in accordance with foregoing can be tracked as catheter-tracking data, which the diagnostic process can use to determine trends in the blood flow. The diagnostic process is configured to provide catheter-tracking data or the trends determined therefrom as input to the display server for output to the GUI of the display screen. The output to the GUI provides a clinician an indication of location of the catheter tube 12 in a vasculature of a patient.

Further in accordance with the catheter-tracking function, the diagnostic process can be configured to determine malposition of the catheter tube 12 in a vasculature of a patient in accordance with temperature data from a secondary temperature sensor disposed within the catheter tube 12 proximal of the primary temperature sensor set forth above. The temperature data from the secondary temperature sensor indicates the blood temperature of the patient when the catheter tube 12 is moved or oriented against blood flow. The temperature data from the secondary temperature sensor indicates an elevated blood temperature when the catheter tube 12 is moved with the blood flow on account of the primary temperature sensor being at the set number of degrees above the blood temperature. Information regarding the blood temperature or elevated blood temperature can be provided as discrete or continuous input to the display server for output to the GUI of the display screen. The output to the GUI provides a clinician an indication of malposition of the catheter tube 12 in a vasculature of a patient.

Notwithstanding the foregoing, malposition of the catheter tube 12 can also be determined by a change in blood flowrate about the primary sensor by way of the blood-flowrate algorithm.

The one or more functions of the diagnostic process can include an ECG function for processing ECG data. As set forth above, the catheter assembly 50 can include the ECG sensor 34. Alternatively, the diagnostic system further includes an electrocardiogram ("ECG") stylet configured to be disposed in the catheter tube 12. The ECG function is for processing the ECG data from the ECG sensor 34 or the ECG stylet while the catheter tube 12 with the ECG sensor 34 or the ECG stylet disposed therein is disposed in a vasculature of a patient. The ECG function confirms location of the distal end 13 or tip of the catheter tube 12, monitors migration of the tip of the catheter tube 12, determines heart rate, or a combination thereof. The ECG function of the diagnostic process can be used to confirm catheter-tip location during catheter-tube placement, monitor for catheter-tip migration, or measure heart rate for the cardiac-parameter function of the diagnostic process.

Various functions of the diagnostic process can be used together to provide clinical data for patient monitoring. This is particularly useful when the diagnostic system 2400 is coupled to an infusion system or a patient monitoring system. With respect to the infusion system, for example, the diagnostic system 2400 can be configured to provide the clinical data for correlation with medication-infusion data for patient response to the infusion of the medication. Temperature, blood flowrate, and cardiac output data could subsequently be trended with data for medication-infusion rates, the foregoing data can be uploaded to an electronic medical record or patient data database, then the data can be used with artificial-intelligence algorithms to improve patient care.

Methods

A method of the diagnostic system 2400 includes an instantiating step of instantiating in the memory 2406 (e.g., the primary memory 2408) of the console 2402 the diagnostic process having the one or more functions for at least processing the temperature data.

The method also includes a sending step of sending the temperature data from the temperature sensor 100 or any temperature sensor of the plurality of temperature sensors 1001, 100*b*, ..., 100*n* to the console 2402 from the catheter assembly 50. The method also includes a loading step of loading the temperature data in the memory 2406 (e.g., the primary memory 2408). The method also includes a processing step of processing the temperature data with the processor 2404 of the console 2402 in accordance with the one or more functions for processing the temperature data.

The method also includes a displaying step of displaying in the GUI on the display screen 2414 configured to communicate with the console 2402 at least a temperature reading associated with any temperature sensor of the catheter assembly 50 while disposed within a vasculature of a patient.

The method can include a monitoring step of monitoring blood flowrate about any temperature sensor of the catheter assembly 50 disposed within the vasculature of the patient with the blood-flowrate function utilizing the blood-flowrate algorithm. Again, the blood flowrate is proportional to an amount of power required to maintain a temperature-sensor temperature at a set number of degrees above blood temperature.

The diagnostic systems and methods disclosed herein provides valuable clinical data to clinicians by integrating sensor(s) into vascular access devices. This eliminates the need for placing additional vascular devices into patients and reduces risks of patient infection and other complications. In addition, the diagnostic systems disclosed herein provide additional data and features not currently present in such additional vascular devices already on the market, such as quality of blood flow around the vascular devices, compliance monitoring of flushing protocol, and monitoring of position of the vascular devices relative to vessel junctions.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A diagnostic system, comprising:
a catheter assembly including:
a catheter tube defining at least one lumen extending between a proximal end and a distal end;
a hub operably attached to the catheter tube;
an extension leg operably attached to the hub, the hub and the extension leg defining at least one fluid passageway in fluid communication with the at least one lumen of the catheter tube; and
a plurality of temperature sensors disposed within the catheter tube including a primary catheter-tube temperature sensor and a secondary catheter-tube temperature sensor proximal of the primary catheter-tube temperature sensor for determining malposition of the catheter tube in a vasculature of a patient, each temperature sensor of the primary and secondary catheter-tube temperature sensors configured for temperature measurement in the catheter tube;
a console configured to communicate with the catheter assembly, the console including memory, a processor, and a proportional-integral-derivative (PID) controller, wherein the PID controller is configured to maintain the primary catheter-tube temperature sensor at a set temperature, and monitor an amount of power utilized in maintaining the primary catheter-tube temperature sensor at the set temperature, wherein the amount of power utilized is proportional to blood flowrate, and wherein blood flowrate is indicative of catheter placement or catheter malposition, and
wherein the processor is configured to measure a blood temperature with the secondary catheter-tube temperature sensor as the catheter tube is moved through the vasculature, wherein a first blood temperature indicates movement in a direction against blood flow, wherein a second blood temperature elevated in relation to the first blood temperature indicates movement in a direction with blood flow, and wherein determining whether the catheter tube is moving in the direction against blood flood or in the direction with blood flow is indicative of the catheter placement or the catheter malposition; and
a display screen configured to communicate with the console, the display screen configured to display a graphical user interface ("GUI") including at least a temperature reading associated with the plurality of temperature sensors.

2. The diagnostic system of claim 1, wherein the console is configured to instantiate a display server configured to coordinate input to the console and output from the console, the output including the GUI.

3. The diagnostic system of claim 1, wherein the memory includes instructions for processing the temperature measurement from any of the plurality of temperature sensors of the catheter assembly while the catheter tube is disposed in the vasculature of the patient.

4. The diagnostic system of claim 1, wherein each temperature sensor of the plurality of temperature sensors is disposed in a different location of a plurality of locations along a length of the catheter tube for measuring a local temperature.

5. The diagnostic system of claim 4, wherein the memory includes instructions for monitoring local temperature changes or trends thereof of the plurality of temperature sensors or the temperature sensors respectively at one or more locations of plurality of the locations.

6. The diagnostic system of claim 1, wherein the processor is configured to provide a console-based alert when a flushing-compliant temperature change does not occur at the primary catheter-tube temperature sensor, the secondary catheter-tube temperature sensor, or both the primary catheter-tube temperature sensor and the secondary catheter-tube temperature sensor as expected from room-temperature flushate being flushed through the catheter assembly after patient-temperature blood is drawn from the catheter assembly or at recommended intervals or instances.

7. The diagnostic system of claim 1, wherein the PID controller is communicatively coupled to the primary catheter-tube temperature sensor, and wherein the set temperature is a set number of degrees above the blood temperature.

8. The diagnostic system of claim 1, wherein a plurality of electrodes are disposed concentrically on the catheter tube, wherein the plurality of electrodes are employed to obtain volumetric measurements resulting in a determination of a size of a vessel in which the catheter tube is disposed.

9. The diagnostic system of claim 8, wherein the GUI provides an indication of a location of the catheter tube in the vasculature of the patient.

10. The diagnostic system of claim 1, further comprising an electrocardiogram ("ECG") stylet or leads embedded within the catheter assembly, wherein the ECG stylet or leads obtain ECG data while the ECG stylet is disposed in the catheter tube and the catheter tube is disposed in the vasculature of the patient to confirm location of a tip of the catheter tube, monitor migration of the tip of the catheter tube, determine heart rate, or a combination thereof.

* * * * *